United States Patent [19]

Stott et al.

[11] Patent Number: 4,816,252

[45] Date of Patent: Mar. 28, 1989

[54] PRODUCT AND PROCESS FOR TRANSFERRING PASSIVE IMMUNITY TO NEWBORN DOMESTIC ANIMALS USING ULTRAFILTERED WHEY CONTAINING IMMUNOGLOBULINS

[75] Inventors: Gerald H. Stott, Emmett, Id.; Dave Lucas, Tucson, Ariz.

[73] Assignee: Protein Technology, Inc., Minneapolis, Minn.

[21] Appl. No.: 818,610

[22] Filed: Jan. 13, 1986

Related U.S. Application Data

[63] Continuation-in-part of Ser. No. 723,612, Apr. 15, 1985.

[51] Int. Cl.$^4$ .................... A61K 39/395; A61K 35/20
[52] U.S. Cl. .................... 424/85.8; 530/416; 530/833; 424/86; 424/87
[58] Field of Search ............ 424/85, 87, 86; 530/416, 833

[56] References Cited

U.S. PATENT DOCUMENTS

| | | | |
|---|---|---|---|
| 2,699,599 | 2/1954 | Reid | 260/112 |
| 3,128,230 | 4/1964 | Heinbach | 424/85 X |
| 3,234,199 | 2/1966 | Reid | 260/112 |
| 3,376,198 | 4/1968 | Peterson et al. | 167/78 |
| 3,487,064 | 12/1969 | Swanson et al. | 260/112 |
| 3,547,900 | 12/1970 | Dienst et al. | 260/112 |
| 3,553,317 | 1/1971 | Michaelson et al. | 424/87 |
| 3,687,682 | 8/1972 | Scheder | 99/57 |
| 3,687,928 | 8/1972 | Brouwer et al. | 260/122 |
| 3,707,770 | 1/1973 | Timmins et al. | 99/116 |
| 3,791,283 | 2/1974 | Moreno et al. | 99/57 |
| 3,896,241 | 7/1975 | Malaspina et al. | 426/271 |
| 3,911,108 | 10/1975 | Singh | 424/86 |
| 3,930,039 | 12/1975 | Kiupers | 426/271 |
| 3,969,336 | 7/1976 | Criswell | 260/112 |
| 3,969,337 | 7/1976 | Lauer et al. | 260/112 |
| 3,975,517 | 8/1976 | Wilson | 424/87 |
| 4,018,752 | 4/1977 | Buhler et al. | 530/833 X |
| 4,028,317 | 6/1977 | Chang | 260/112 |
| 4,042,575 | 8/1977 | Eustache | 426/583 X |
| 4,042,576 | 8/1977 | Eustache | 260/112 |
| 4,051,235 | 9/1977 | Plymate | 424/85 |
| 4,100,149 | 7/1978 | Meiller et al. | 260/112 |
| 4,229,342 | 10/1980 | Mirabel | 260/120 |

(List continued on next page.)

FOREIGN PATENT DOCUMENTS

| | | |
|---|---|---|
| 60-70038 | 4/1985 | Japan . |
| 60-75433 | 4/1985 | Japan . |
| 61-289846 | 12/1986 | Japan . |
| 61-289845 | 12/1986 | Japan . |
| 1202979 | 8/1970 | United Kingdom .................. 424/88 |
| 1573995 | 9/1980 | United Kingdom . |

OTHER PUBLICATIONS

*Physiological Effects of the Colostral Peptide, Colostrokinin, and Inanition on Immunoglobulin Absorption and Adrenal/Thyroid Response in the Bovine Neonate*, T. G. Schlagheck, A Dissertation Submitted in Partial Fulfillment of the Requirements for the Degree of Doctor of Philosophy in the Graduate College of the University of Arizona (1983).

(List continued on next page.)

Primary Examiner—Howard E. Schain
Attorney, Agent, or Firm—Cahill, Sutton & Thomas

[57] ABSTRACT

The present invention relates to a product and process for assuring the transfer of adequate passive immunity to newborn domestic animals. Immunologically active immunoglobulins are extracted from the whey byproduct of dairy manufacturing by using ultrafiltration techniques to separate the large immuoglobulin molecules from the whey. The ultrafiltration retentate is dried to produce a filtered product having a high concentration of immunoglobulins. The dry filtered product is assayed to verify the immunological activity of the product and to measure the distribution and concentration of pathogen specific antibodies. The dry filtered product is stored. Subsequently, a dose of the product containing at least a minimum weight ratio of immunologically active Ig is fed to the newborn animal to transfer passive immunity. Ion exchange techniques can be combined with ultrafiltration techniques to significantly increase the Ig concentration in the ultimate product while simultanously reducing the net cost of producing the product. They whey-derived product may also be used on a continuous basis as a food supplement for an animal to enable the immunologically active immunoglobulin molecules in the product to attack pathogens present in the digestive system of the animal.

33 Claims, 2 Drawing Sheets

U.S. PATENT DOCUMENTS

| | | | |
|---|---|---|---|
| 4,265,294 | 5/1981 | Buhler et al. | 426/582 |
| 4,322,275 | 3/1982 | Jain | 204/180 |
| 4,324,782 | 3/1982 | Beck | 424/87 |
| 4,376,072 | 3/1983 | Connolly | 260/120 |
| 4,377,569 | 3/1983 | Plymate | 424/85 |
| 4,402,938 | 9/1983 | Collins et al. | 424/85 |
| 4,436,658 | 3/1984 | Peyrouset et al. | 260/122 |
| 4,485,040 | 11/1984 | Roger et al. | 260/122 |
| 4,490,290 | 12/1984 | Gani et al. | 260/112 |
| 4,528,203 | 7/1985 | Harris et al. | 530/833 X |
| 4,582,580 | 4/1986 | Goudal | 204/182.6 |
| 4,623,541 | 11/1986 | Elliot | 424/85 |
| 4,644,056 | 2/1987 | Kothe | 530/387 |

OTHER PUBLICATIONS

*The Effects of Passive Immunity on Growth and Mortality in the Dairy Heifer*, J. D. Robison, A 1984 Dissertation Submitted in Partial Fulfullment of the Requirement for the Degree of Doctor of Philosophy in The Graduate College of the University of Arizona.

*Characterization of Monoclonal Antibodies to Bovine IgG1*, W. A. Fleenor, D. O. Lucas, G. H. Stott and A. J. Guidry, Veterinary Immunology and Immunopathology, 6(1984) 365–378 Elsevier Science Publishers B. V., Amsterdam—Printed in the Netherlands.

*Colostral Immunoglobulin Absorption Linearly Related to Concentration for Calves*, G. H. Stott and A. Fellah, Dept. of Animal Science, U. of A., 1983 J. Dairy Sci. 66:1319–1328.

*Quantification of Bovine IgG, IgM and IgA Antibodies to Clostridium Perfringens B-Toxin by Enzyme Immunoassay I. Preparturient Immunization for Enhancement of Passive Transfer of Immunity*, W. A. Fleenor and G. H. Stott, Dept. of Animal Science, U. of A., Veterinary Immunology and Immunopathology, 4 (1983) 579–591, Elsevier Science Publishers B. V., Amsterdam—Printed in the Netherlands.

*Colostral Immunoglobulin Concentration in Two Fractions of First Milking Postpartum and Five Additional Milkings*, G. H. Stott, W. A. Fleenor and W. C. Kleese, Dept. of Animal Science, U. of A., 1981 J. Dairy Sci 64: 459–465.

*Effect of Suckling Followed by Bottle Feeding Colostrum on Immunoglobulin Absorption and Calf Survival*, T. J. Bringnole and G. H. Stott, Dept. of Animal Sciences, U. of A., 1980 J. Dairy Sci 63: 451–456.

Colostral Immunoglobulin Transfer in Calfs II, The Rate of Absorption, G. H. Stott, D. B. Marx, B. E. Menefee and G. T. Nightengale, Dept. of Animal Sciences and Center for Quantitative Studies, U. of A., 1979 J. Dairy Sci. 62: 1766–1773.

*Nutritional and Biochemical Studies of Whey Products*, E. Forsum and L. Hambraeus, Institute of Nutrition, University of Uppsala, J. Dairy Sci 60: 370–377.

*Use of Ultrafiltration/Reverse Osmosis Systems for the Concentration and Fractionation of Whey*, R. I. Fenton-May and C. G. Hill, Jr., Dept. of Chemical Engineering, Univ. of Madison Wisconsin and C. H. Amundson, Dept. of Food Science, Univ. of Madison, Wisconsin 14–Journal of Food Sciences—vol. 36 (1971).

*Nomenclature of Proteins of Cow's Milk: Fifth Revision*, W. N. Eigel, J. E. Butler, C. A. Ernstrom, H. M. Farrell, Jr., V. R. Harwalkar, R. Jenness, R. McL. Whitney, 1984 J. Dairy Sci 67: 1599–1631.

*Antibody to Human Rotavirus in Cow's Milk*, R. H. Yolken, MD, G. A. Losonsky, MD, S. Vonderfecht, DVM, PhD, Flora Leister, BA, and Siok-Bi Wee, MS, The New England Journal of Medicine, Mar. 7, 1985.

*Preparation of Bovine Immunoglobulins and Free Secretory Component and Their Specific Antisera*, J. E. Butler and C. F. Maxwell, J. Dairy Sci 55: 151.

Advertisement: The Genecol 99 Story . . . How to Reduce the Death Losses Caused by *E. Coli* Scours.

*Protection of Calves Against Fatal Enteric Colibacillosis by Orally Administered Escherichia Coli K99-Specific Monoclonal Antibody*, D. M. Sherman, D. D. Acres, P. L. Sadowski, J. A. Spring, B. Bray, T. J. G. Raybould and C. C. Muscoplat, Infection and Immunity (Nov. 1983) 42: 563–658.

Trends in Whey Fractionation and Utilization, A Global Perspective, Roger, Zall, Dept. of Food Science, 16 J. Dairy Sci 67: 2621–2629.

*Review of Processes and Products for Utilization of Lactose in Deproteinated Milk Serum*, P. G. Hobman, New Zealand Dairy Research Institute, 1984 J. Dairy Sci. 67: 2630–2653.

*Whey Protein Recovery Processes and Products*, M. E. Matthews, Rangitaiki Plains Dairy Company 1984 J. Dairy Sci 67: 2680–2692.

*Symposium: Assessing Functionality of Whey Proteins—Critical Aspects in Development of Whey Protein Concentrate*, Nicholas Melochouris, Stauffer Chemical Company, 1984 J. Dairy Sci. 67: 2693–2700.

*Effects of Various Heat Treatments on Structure and Solubility of Whey Proteins*, J. N. deWit and G. Klarenbeek, Netherlands Institute for Dairy Research 1984 J. Dairy Sci 67: 2701–2710.

Article Title: "Studies on Replacement Colostrum for Piglets", Date of Publication: May 19, 1976, Source: Japanese Journal of Swine Reserch 16.1:1–12 (Partial Translation of Selected Sections of Article), Authors: A. Takahashi; T. Abe; T. Moriji; S. Maeda; K. Himeno and S. Nakano.

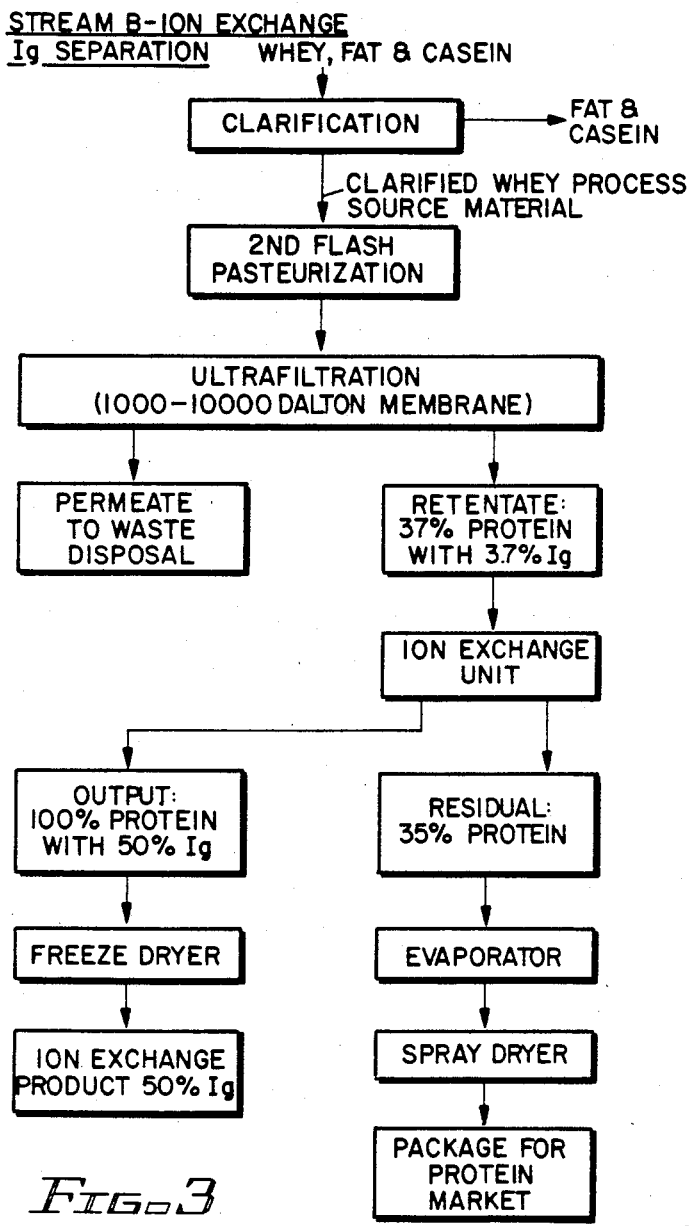

PRODUCT AND PROCESS FOR TRANSFERRING PASSIVE IMMUNITY TO NEWBORN DOMESTIC ANIMALS USING ULTRAFILTERED WHEY CONTAINING IMMUNOGLOBULINS

This application is a Continuation-in-Part patent application of U.S. patent application Ser. No. 6/723,612, filed Apr. 15, 1985, now abandoned.

BACKGROUND OF THE INVENTION

1. Field of the Invention

This invention relates to a product and process for controlling the transfer of passive immunity to newborn domestic animals such as calves, and more particularly, to the use of ultrafiltration techniques or combined ultrafiltration and ion exchange techniques to extract immunoglobulin molecules from lactoserum such as whey to produce a highly concentrated immunologically active product which can be fed to newborn animals under controlled conditions to achieve passive immunity.

2. Description of the Prior Art

As is common with most domestic animals, bovine calves are born without immunity. Passive immunity is transferred on a postpartum basis from a dam (mother) to the newborn calf through an initial mammary gland secretion known as colostrum. As illustrated by FIG. 1, this initial colostrum secretion contains rapidly diminishing levels of immunologically active, large molecular weight proteins known as immunoglobulins (abbreviated below as "Ig"). These Ig molecules possess antibody properties, are actively produced by mature animals, and enhance immunity to infection by bacteria, viruses or parasites. At birth, a calf lacks Ig in its blood serum. Only as a direct response to ingestion and absorption of a quantity and quality of Ig from maternal colostrum shortly after birth can a calf's immune system function efficiently.

The first essential element of the natural passive immunity transfer mechanism relates to the characteristics of the maternal colostrum. To achieve ideal passive immunity, the maternal colostrum should contain an adequate concentration of Ig having an appropriate distribution of pathogen specific antibodies and an appropriate concentration of each pathogen specific antibody. If the maternal colostrum contains an insufficient concentration of important pathogen specific antibodies, the calf will absorb an insufficient quantity of these antibodies and will develop a deficient level of immunity to the diseases which such antibodies attack.

The second essential element of the natural passive immunity transfer mechanism is calf-oriented and relates to the quantity and time of colostrum ingestion. As to quantity of ingestion, previous studies have indicated that there is a limit to the volume of colostrum that can be ingested to maximize the level of Ig absorbed into the calf's circulatory system. Consumption of more than two liters of colostrum fails to enhance calf Ig absorption levels to any significant degree. Furthermore, newborn calves rarely ingest more than two liters of liquid within a feeding period. As to the time of ingestion, FIG. 2 illustrates that the permeability of the newborn calf's gut to the large molecular weight Ig molecules diminishes very rapidly after birth as a result of intestinal cell maturation. This well-known natural intestinal mechanism may be referred to as the "critical period of absorption" which defines the short postpartum interval during which the calf must consume and absorb the optimum quantity of ideal potency colostrum to achieve an ideal level of passive immunity. Although colostrum consumption as late as twenty-four hours postpartum may achieve some immune transfer, subsequent colostrum consumption will have very little effect on passive immune levels. Ideally, colostrum ingestion should occur within the first eight hours postpartum.

In practice, a high percentage of calves either consume far less than an ideal quantity and quality of colostrum or fail to consume colostrum within the critical absorption period. The resulting adverse effects due to the lack of immune transfer are demonstrated by high calf death rates, increased susceptibility to disease and reduced growth rate.

FIG. 3 charts calf blood serum Ig concentration versus time to illustrate the passive immunity transfer mechanism described above under absolutely ideal conditions which rarely occur in nature. At birth, a calf lacks immunity to disease as is demonstrated by the low blood serum antibody concentration. Within approximately six to twelve hours after birth as indicated by reference number 1, the calf ingests two liters of colostrum having an ideal Ig concentration and distribution of pathogen specific antibodies. As these large molecular weight Ig or antibody molecules are intestinally absorbed, the blood serum antibody concentration rapidly increases as indicated by the upwardly sloping line designated by reference number 2. At the time several hours after initial colostrum ingestion designated by reference number 3, the transfer of colostrum Ig molecules from the gut into the calf's bloodstream has been completed. Over the next few days, the blood serum Ig concentration derived from the maternal colostrum gradually declines through normal systemic turnover. Following the time indicated by reference number 4, the calf's immune system commences active Ig production which replaces the declining supply of colostrum-derived Ig. By the time indicated by reference number 5, the calf's immune system achieves a self-sustaining or active Ig production and will maintain an essentially constant blood serum Ig concentration.

Previous research has indicated that a blood serum Ig concentration on the order of twenty milligrams per milliliter or above is highly desirable. Calves possessing such Ig concentrations demonstrate a markedly reduced mortality rate, a high level of resistance to disease and impressively enhance growth rates in comparison to calves having lower levels of passive immunity.

The dramatic contrast between an ideal immunity transfer as illustrated in FIG. 3 and common naturally occuring immunity transfer is illustrated in FIG. 4. Consumption of an insufficient quantity of colostrum or consumption of low Ig concentration colostrum as described in the following paragraph produces a passive immunity transfer curve analogous to that designated by reference number 6 in FIG. 4. If a calf having this deficient level of passive immunity is exposed to a disease, there is a high probability that it will contract the disease, require expensive medical treatment and may die or lack sufficient growth potential.

Because domestic dairy cattle have been selectively bred for maximum milk production, the passive immunity transfer problems encountered by dairymen are particularly acute. At the onset of lactation, a dairy cow's high milk production volume rapidly dilutes the limited quantity of colostrum Ig molecules. As a result, the concentration of these Ig molecules in the fluid initially consumed by a newborn calf may be far below the level required to achieve an adequate level of passive immunity. Since the typical non-aggressive dairy calf consumes only a comparatively small amount of colostrum during the critical absorption period, the number of Ig molecules present in the calf's gut and available for absorption into the bloodstream is frequently unacceptably low. The resulting passive immunity level fails to provide adequate disease resistance.

To combat the immunity deficiency problems outlined above, some dairymen having small dairy herds manually milk what they believe to be an adequate quantity of colostrum from a dam and force feed it to its newborn calf during the critical absorption period. This labor intensive method of controlling the timing and quantity of colostrum consumption cannot compensate for colostrum having a low Ig concentration or an inadequate spectrum of pathogen specific antibodies. Since only complex, time consuming laboratory tests can measure the colostrum Ig concentration and antibody distribution, these dairymen have no way of verifying that the colostrum which they laboriously obtain and force feed to newborn calves will provide adequate levels of passive immunity.

In large dairy operations, a different tactic has been implemented in an attempt to control the time of colostrum ingestion, the quantity of Ig consumed and the pathogen specific antibody distribution of the colostrum. Milk drawn from a group of dams within twelve hours postpartum is blended together. An appropriate quantity of this blended "colostrum" is fed to each newborn calf. Because dairymen have no way of controlling the Ig concentration or distribution of pathogen specific antibodies in this blended "colostrum," this labor intensive procedure has not achieved satisfactory results.

Another existing technique for enhancing the disease resistance of a calf to a specific disease involves prepartum vaccination of the dam. The vaccination increases the serum blood level concentration of the desired pathogen specific antibody and ultimately yields colostrum having enhanced levels of the desired antibody. After consuming this enhanced colostrum, the calf attains an increased level of immunity, but only to the selected disease. Besides the obvious risk to the dam, vaccination procedures are time critical and expensive.

In laboratory studies, researchers have assayed the Ig concentration and distribution of pathogen specific antibodies in colostrum and have administered controlled quantities of such assayed colostrum to newborn calves at controlled times within the critical absorption period. A direct correlation between these measured colostrum Ig variables and calf disease resistance, death rate, and growth rate has been demonstrated. Although these laboratory testing activities have substantially increased the level of knowledge of the natural passive immunity transfer mechanism in animals, they have not solved the immunity transfer problems outlined above by providing a method for positively controlling the Ig concentration and distribution of pathogen specific antibodies in colostrum.

The substantial economic loss suffered by dairymen and others as a direct result of the inability to control the passive immunity transfer mechanism, even in view of a complete comprehension of the operation of that natural mechanism, evidences a strong need for a product or process capable of positively controlling the immunity transfer mechanism. In an attempt to satisfy this need, a genetic engineering firm has recently introduced an artificially synthesized Ig molecule which includes a single antibody pathogen specific to enterotoxigenic *E. coli*, a bacterium which induces a diarrhea condition in calves known as scours. Scours commonly affects newborn calves and lead to rapid, uncontrollable dehydration and frequent death. This synthesized product is administered orally within twelve hours postpartum and is capable of producing increased immunity only to that specific *E. coli* bacterium.

It is therefore a major object of the present invention to provide a process for extracting naturally occurring Ig molecules from milk or whey to produce a highly concentrated immunologically active product which can subsequently be dissolved in a fluid to produce a colostrum substitute or supplement having a controlled Ig concentration and a known distribution and concentration of numerous desirable pathogen specific antibodies.

It is another major object of the present invention to provide a process for controlling the natural passive immunity transfer mechanism by feeding a controlled quantity of the whey-derived product to newborn animals within the critical absorption period to achieve a designated blood serum concentration of each of a broad spectrum of identified pathogen specific antibodies to provide enhanced levels of passive immunity to selected diseases without reliance on consumption of natural colostrum.

Another major object of the present invention is to derive said product from whey, a low economic value dairy manufacturing byproduct.

Another object of the present invention is to provide a process for producing said whey-filtered product by using commercially available equipment common in dairy manufacturing plants.

Another object of the present invention is to provide a process for producing said whey-derived product in large quantities at an affordable, cost effective price.

Another object of the present invention is to provide said whey-derived product in a dry powder form which can be stored for a substantial period of time.

Another object of the present invention is to provide a process for producing said product from milk obtained from a group of animals having an enhanced level of immunity to a specific disease and feeding said product to calves born into another herd which requires an enhanced level of immunity to that same disease.

It is still another object of the present invention to provide said whey-derived product which can be administered to a newborn calf in a quantity directly related to the calf's needs, according to size, to provide passive immunity.

Briefly stated, the present invention encompasses a process for extracting immunologically active immunoglobulins from milk. The milk is initially processed into whey. Ultrafiltration of the whey produces a retentate having an increased concentration of immunoglobulins. The residual liquid components are removed from the ultrafiltration retentate to produce a filtered product having a further increased concentration of immunoglobulins. Each step in the process is executed under conditions which substantially maintain the immunological activity of the immunoglobulins. The filtered product is subsequently dissolved in a liquid such as colostrum, milk or water to achieve a desired Ig concentration. This Ig solution is ingested by a newborn domestic animal such as a calf postpartum within the critical absorption period. Ion exchange techniques may be implemented to further process an ultrafiltration retentate to significantly increase the concentration of immunologically active Ig in the whey-derived product. This higher concentration Ig product may be blended with a relatively lower Ig concentration filtered product to yield a product having a substantially increased Ig concentration in comparison to Ig concentration levels attainable through use of ultrafiltration alone.

By implementing the process of the present invention, passive immunity can be transferred to a newborn domestic animal under controlled conditions, ensuring an adequate level of passive immunity to a broad spectrum of disease.

DESCRIPTION OF THE DRAWINGS

The invention is pointed out with particularity in the appended claims. However, other objects and advantages together with the operation of the invention may be better understood by reference to the following detailed description taken in connection with the following illustrations, wherein:

FIG. 4 graphically illustrates non-ideal operation of the natural passive immunity transfer mechanism caused by Ig deficiency in the maternal colostrum. This graph is presented for illustrative purposes only and is not drawn to scale.

FIG. 5 is a flow chart illustrating the process of producing a filtered product having a controlled Ig concentration and distribution of pathogen specific antibodies which can be ingested by a newborn domestic animal to control the transfer of passive immunity.

FIGS. 6A-6D illustrate the production of four different samples of filtered product according to the process of the present invention. Each sample includes a different relative concentration of ten selected pathogen specific antibodies.

FIG. 7 graphically compares the calf blood serum Ig concentration achieved by natural colostrum with the blood serum Ig concentration achieved by whey-derived product produced according to the present invention.

FIG. 8 is a process flow diagram illustrating a revised ultrafiltration process for producing high Ig concentration filtered product.

FIG. 9 is a process flow diagram illustrating a combined ultrafiltration/ion exchange process for separating immunologically active Ig molecules from whey.

FIG. 10 is a process flow diagram illustrating the manner in which filtered product from the Stream A process depicted in FIG. 8 is combined with highly concentrated Ig material from the Stream B ion exchange unit depicted in FIG. 9 to produce a blended product having an Ig concentration level substantially above levels achievable through use of ultrafiltration alone.

FIG. 11 illustrates the composition of the whey protein fraction.

DESCRIPTION OF THE PREFERRED EMBODIMENT

In order to better illustrate the advantages of the invention and its contributions to the art, a preferred embodiment of the inventive process and product will now be described in detail.

Figure 1:
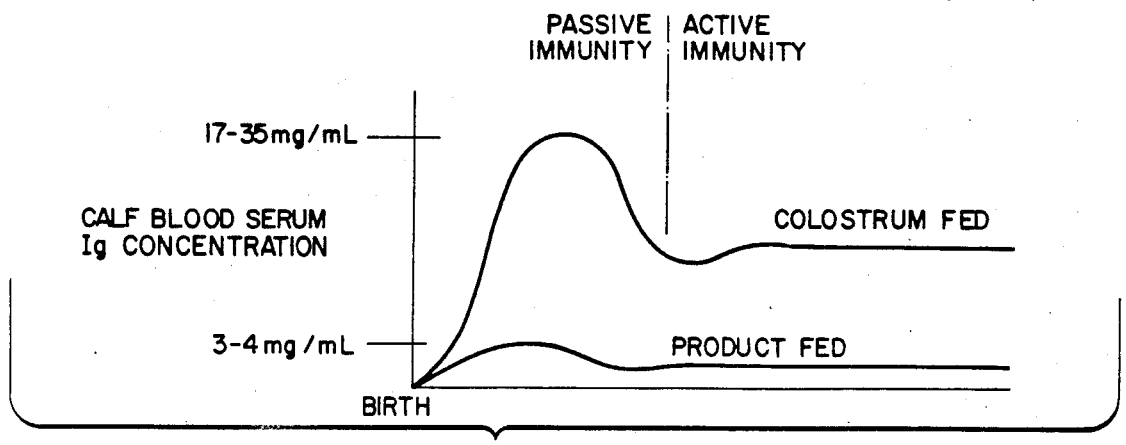
FIG. 1 is a graph illustrating the rapid decrease in maternal colostrum Ig concentration following the onset of lactation. This graph has not been drawn to scale but is intended to generally illustrate the rapid postpartum decrease in Ig concentration available to a newborn calf.

As indicated by FIG. 1, milk secreted by domestic animals such as dairy cows includes long term but low level concentrations of Ig which has no measurable effect on passive immunity when ingested. The present invention relates to a process for extracting and concentrating the Ig molecules found in milk under carefully controlled conditions to preserve the immunological activity of the structurally delicate, thermosensitive Ig molecules. Such concentrated, immunologically active Ig molecules can then be fed to newborn calves shortly postpartum as either a colostrum substitute or supplement to exert positive control over the natural passive immunity transfer mechanism. The invention recognizes and takes advantage of the fact that Ig molecules constitute the largest molecules in milk and that a limited number of these molecules remain in the low economic value whey byproduct of the cheese making process. Although appoximately 85,000,000 metric tons of whey is created annually as a byproduct of cheese production worldwide, about 34,000,000 metric tons of whey cannot be economically utilized. The whey byproduct useful in practicing the present invention can therefore be obtained at minimal cost and will reduce the burden of disposing the unwanted whey.

The upper section of the FIG. 5 process flow chart indicates that in a conventional cheese production facility, raw milk is processed to create curd, the primary cheese constituent, and a liquid whey byproduct. The raw milk input product includes approximately fourteen percent solids. Four percent constitutes proteins, the largest of which include the sought after Ig molecules. A high percentage of the milk protein component is precipitated out as casein during the cheese making process. The resulting whey byproduct includes approximately six percent solids, seventy percent of which represents lactose and thirty percent of which represents proteins, minerals and fat. The residual whey protein component in general comprises a mixture of lactalbumin, lactoglobulin, serum albumin, immunoglobulins (Ig) and polypeptides. One liter of whey contains approximately five grams of protein of which only about 0.5 gram represents Ig, the protein responsible for transferring passive immunity to a calf.

An objective of the present invention is to process raw milk and the resulting whey byproduct under carefully controlled conditions to radically increase the Ig concentration of the ultimate processed product in comparison to the minimal, immunologically ineffective Ig concentration in the raw milk input product. This process must be accomplished under carefully controlled conditions to avoid substantially reducing the immunological activity of the Ig molecules.

Numerous prior art techniques exist for producing dry concentrated protein extract from whey. This protein extract is commonly referred to as whey protein concentrate or "WPC." Such prior art protein extraction and concentration techniques are primarily concerned with preserving the food qualities of the WPC, e.g., taste, flavor, solubility, etc. Although these prior art whey and WPC extraction techniques are capable of producing useful food products, they almost universally destroy or substantially reduce the immunological activity of Ig molecules in WPC by exposing the raw milk, whey or resulting WPC to: (1) excessive thermal (time/temperature) conditions, (2) excessive bacterial activity, or (3) excessive enzymes added in processing or resulting from such bacterial activity.

Referring now to FIG. 5, the specific process steps capable of separating Ig molecules from raw milk and producing an end product having highly concentrated levels of immunologically active Ig will now be discussed in detail.

A homogeneous volume of raw milk is typically obtained from one or more herds of dairy cattle located within a specific geographic region. This raw milk is flash pasteurized, for example, by rapidly elevating its temperature to approximately 160° F., maintaining it at that temperature for from fifteen seconds to as long as twenty seconds, and rapidly decreasing the milk temperature. Testing has indicated that the comparatively rapid temperature rise, the short time at elevated temperatures and the comparatively rapid temperature reduction accomplished during this flash pasteurization step adequately standardizes and controls microbial activity in the milk without significantly affecting the imunological activity of the Ig in the milk.

If significant deviations are made from the above-stated flash pasteurization time/temperature parameters as is common with other well known but longer duration pasteurization procedures, the immunological activity of the milk Ig molecules will be substantially reduced or destroyed. Such procedures should therefore be avoided while practicing the process of the present invention.

In certain instances, it is possible to implement a second flash pasteurization step during whey processing operations. The implementation of a second flash pasteurization step will tend to reduce the overall immunological activity of the Ig molecules, but still results in a useful level of Ig immunological activity. The utilization of a third flash pasteurization step has been found to virtually totally destroy the immunological activity of the Ig molecules and should therefore be avoided in most circumstances. The immunological activity of the Ig molecules should be carefully tested following each pasteurization step during the initial implementation of the inventive process to verify continuing Ig immunological activity. The results of such testing will indicate whether any pasteurization step should be modified or eliminated.

After completion of the pasteurization step, the milk is exposed to an appropriate cheese producing starter such as lactobacillus. As is common practice in cheese processing, the temperature in the cheese formation vat is generally adjusted to and maintained at about 86° F. to 90° F. for approximately two hours until a desired degree of curd formation has occurred. At that time, the cheese vat temperature is increased to approximately 102° F. and the whey is drained off, a procedure typically requiring approximately thirty to forty-five minutes. The whey byproduct is immediately transferred to a clarifier or separator at a temperature of about 100° F. where the fat and casein particle components of the whey byproduct are removed. At this point, the clarified whey may be stored temporarily at 40° F. to restrict bacterial activity or may be immediately transported to an ultrafiltration system. During ultrafiltration, the whey is heated to and maintained at a temperature of between about 120° F. to 130° F. The specific process parameters recited above have been found to substantially maintain Ig immunological activity. In implementing the process of the present invention, the above-stated time and temperature parameters may be varied as necessary as long as the Ig immunological activity is substantially maintained as verified by test procedures of the type described below.

Ultrafiltration techniques have been utilized for a number of years to separate the various groups of larger molecular weight protein molecules from the smaller molecular weight, nonprotein components of clarified whey. Similar ultrafiltration techniques are followed in implementing the process of the present invention. The warm clarified whey is directed to a first ultrafiltration module designated in FIG. 5, as "$UF_1$." In one embodiment, module $UF_1$ includes an ultrafiltration membrane permeable to materials having a molecular weight less than about ten thousand Daltons, but impermeable to higher molecular weight materials such as protein molecules. The material retained by the ultrafiltration membrane is referred to as the "retentate," while the material passing through the ultrafiltration membrane is referred to as the "permeate." Undesirable lower molecular weight materials such as lactose, minerals and salts are permeable to the ultrafiltration membrane and are removed from the whey by-product along with water during the initial ultrafiltration steps.

As the retentate is passed either repeatedly through a single ultrafiltration module or directed to the next in a series of ultrafiltration modules, it becomes more concentrated with solids, its viscosity increases and a polarization phenomenon occurs at the ultrafiltration membranes, rendering them ineffective. Membrane polarization is counteracted by diluting the retentate with water and subjecting the diluted retentate to further ultrafiltration, a process known as diafiltration. This series of ultrafiltration steps is repeated until the retentate contains solids having highly concentrated levels of proteins, preferably as high as seventy to eighty percent proteins. At this point in the procedure, the concentration of the desired Ig segment of the protein molecules represents less than ten percent of the total retentate protein composition. Since the smallest of these retentate Ig molecules have molecular weights on the order of one hundred and sixty thousand Daltons or greater and since serum albumin, the next largest retentate protein molecule, possesses a molecular weight on the order of sixty-six thousand Daltons, the partially filtered retentate can be directed through one or more ultrafiltation modules having an ultrafiltration membrane permeable to the serum albumin and other lower molecular weight protein molecules and impermeable to the substantially larger Ig molecules to significantly increase the retentate Ig concentration. Ultrafiltration membranes capable of achieving these objectives are available commercially.

Although the ultrafiltration modules depicted in FIG. 5 have been shown as having ultrafiltration membranes with either a ten thousand or one hundred thousand Dalton permeability, such specific permeability levels have been utilized merely for the purpose of illustration. The invention can be implemented in many different ways by repeatedly utilizing a single ultrafiltration module, sequentially substituting membranes having differing permeability levels, utilizing a series of ultrafiltration modules having a series of membranes of either increasing or constant permeability, or by using a single ultrafiltration module having a membrane permeability between about 66,000 to 160,000 Daltons. In practice, an ultrafiltration module having a single 100,000 Dalton membrane has been found to work in a satisfactory manner. In view of the objectives and procedures stated above, selection of appropriate ultrafiltration equipment and procedures would be obvious to one of ordinary skill in the art in order to achieve the desired elevated concentrations of the large molecular weight Ig molecules.

It is important to the practice of the present invention that the immunological activity of the Ig molecules be preserved during all processing steps, including the ultrafiltration steps, by appropriate temperature control, by maintenance of conditions to minimize unwanted microbial activity, and by carefully controlling and monitoring heating and pasteurization. In existing cheese processing plants and ultrafiltration plants, very few if any of these safeguards are followed. As a result, existing ultrafiltration plants produce WPC having an Ig component lacking significant immunological activity.

Since destruction of the immunological properties of Ig molecules may not alter molecular size or weight, it is important to the practice of the present invention that only a comparatively small percentage of Ig molecules be immunologically deactivated. Because the ultrafiltration membrane sorts molecules by size and not by immunological activity, an ultrafiltration retentate resulting from an input material having an excessive concentration of immunologically deactivated Ig molecules will yield an adequate concentration of Ig molecules (both immunologically active and inactive) without achieving the desired concentration of immunologically active Ig molecules. Ingestion of an Ig solution having an excessive concentration of immunologically inactive Ig will fail to achieve an effective blood serum concentration of immunologically active Ig in newborn domestic animals. It is therefore important to maintain a relatively high concentration of immunologically active Ig molecules in comparison to immunologically inactive Ig molecules throughout each step of the inventive process to produce a product capable of controlling the transfer of passive immunity.

Following completion of ultrafiltration, the retentate may be further concentrated by passing it through a reverse osmosis device which includes an osmotic membrane permeable to water molecules and impermeable to other molecules. In implementing the present invention, the reverse osmosis step is advantageous, but not essential. Utilization of the reverse osmosis device substantially reduces the amount of energy consumed during subsequent WPC drying procedures and renders the process more energy efficient.

The partially dehydrated WPC exiting the reverse osmosis device is then dried by conventional freeze-drying procedures (lyophilization) or spray drying techniques. In most situations, the spray drying procedure is preferred since the equipment is commonly found in most dairy processing plants. Furthermore, this procedure is more efficient, drying WPC at substantially greater rates and at lower cost than is possible with freeze-drying. The resulting dry filtered product can be stored at room temperature.

Since the immunological activity of the Ig is easily destroyed by excessive thermal exposure, but is unaffected by low or freezing temperatures, removal of water from the partially dehydrated ultrafiltration retentate by freeze-drying equipment does not adversely affect the immunological activity of the Ig. A different mechanism prevents significant reduction in the immunological activity of the Ig during spray drying. Although in spray drying equipment the partially dehydrated filtration retentate is exposed to high velocity air at a temperature on the order of 300° F., the temperature of the Ig molecules is maintained at a comparatively low level due to the substantial heat sink effect of the water heat of vaporization. Overall, the spray drying procedure is more economical and produces dry powdered WPC at substantially higher rates than is possible with freeze-drying equipment.

Prior art technique for partially drying concentrated protein ultrafiltration retentate to produce WPC for use in animal or human food products frequently involve placement of the retentate in a vacuum chamber maintained at elevated temperatures for periods of six to eight hours. Although the flavor and nutritional properties of the vacuum dried WPC may be uneffected by this procedure, the immunological activity of the Ig is completely destroyed. Such retentate drying techniques are therefore unacceptable in implementing the process of the present invention.

Following the retentate drying step, the dry powdered WPC should be assayed to verify the immunological properties of the resulting Ig, including the distribution and concentration of pathogen specific antibodies in the Ig. The graphs depicted in FIGS. 6A-D plot the relative concentration of pathogen specific antibodies in various samples of dry filtered product produced by implementing the process of the present invention. These graphs are intended to illustrate the sample to sample variations which could result from extracting Ig molecules from different batches of raw milk having differing Ig distributions and concentrations. Although raw milk may contain an unknown number of pathogen specific antibodies and other antibodies, the FIG. 6 graphs illustrate hypothetical variations in ten of these different antibody types which may be used as standards to control the processing parameters and the quality of the resulting product. A hypothetical set of quality control parameters each designated as "minimum acceptable level" has been incorporated into the FIG. 6 graphs to indicate the potential variability of the desired antibody type concentration in comparison to the assayed concentration in different samples of the immunologically active filtered product. In practice, each minimum acceptable antibody level would be carefully determined to ensure at least a predetermined level of passive immunity to a specific disease for a calf fed a measured quantity of filtered product at a designated time postpartum.

In many cases, it would be advantageous to determine quality control standards for the filtered product by randomly sampling colostrum taken from a group of dams and assaying the distribution and concentration of pathogen specific antibodies in each sample. Since within any given sampled group colostrum immunological properties typically vary widely from unacceptably low to optimum levels, an average sample or one of the optimum colostrum samples could be adopted as a quality control standard. Filtered product quality control standards relating to the overall Ig concentration and to the distribution and concentration of identified pathogen specific antibodies could be adapted to correlate with this "standard colostrum."

Alternatively, it may be desirable to adopt a different quality control standard for each of a number of different geographic regions within the United States or elsewhere. A "regionalized standard colostrum" could be determined by obtaining a colostrum sample from a statistically significant number of healthy cows within each region. When pooled together, these colostrum samples will yield an appropriate regionalized standard colostrum which can be assayed to define a standard Ig concentration and a standard distribution and concentration of identified pathogen specific antibodies.

Maternal colostrum characteristics as well as other factors may be considered when determining an appropriate filtered product quality control standard. For example, a selected colostrum sample may be assayed to determine its Ig concentration and the concentration of predetermined pathogen specific antibodies of interest. An appropriate quality control standard for Ig concentration and for each one of a predetermined group of pathogen specific antibodies might be higher or lower than or equal to the assayed concentrations of the selected maternal colostrum sample. Determination of the particular pathogen specific antibodies to be incorporated in a quality control standard and the desired concentration of each selected antibody could be made by a person skilled in the art based on numerous considerations such as existing or anticipated regional disease exposure risks, disease susceptability of specific animal categories or breeds, existing state of health of a specific herd or group of animals and anticipated climatic conditions.

In comparing the filtered product with the selected quality control standard, it is necessary to measure the distribution and concentration of pathogen specific antibodies and to verify that the overall immunological activity of the Ig molecules has been substantially maintained during the entire Ig extraction process. Using presently available technology, two different test procedures may be used in combination to make these determinations.

A preferred test, known as the "EIA" test, is capable of measuring the distribution and concentration of pathogen specific antibodies in the filtered product and is described in an article entitled "Quantification of Bovine IgG, IgM and IgA Antibodies To Clostridium Perfringens B-Toxin By Enzyme Immunoassay I. Preparturient Immunization For Enhancement Of Passive Transfer of Immunity." This article was published in *Veterinary Immunology and Immunopathology*, Vol. 4 (1983) at pp. 579-591 and was authored by W. A. Fleenor and G. H. Stott. The disclosure of that article is hereby incorporated by reference. The EIA test procedure discussed in that article is known to persons of ordinary skill in the appropriate field.

The EIA test in combination with the radial immune diffusion test (RID test) is capable of measuring the percentage of Ig molecules which have been immunologically deactivated during the process of the present invention. Although the RID test is capable of measuring the number of Ig molecules in milk, whey or the filtered product, it cannot distinguish between immunologically active and immunologically inactive Ig molecules.

It is therefore necessary to perform a dual analysis of the milk or whey input product by (1) using the EIA test to assay the distribution and concentration of pathogen specific antibodies in the input product and (2) using the RID test to measure the number of IG molecules in the input product. The EIA test results divided by the RID test results yield a first set of ratios representative of the relative concentration of each tested pathogen specific antibody to the total number of IG molecules in the input product, whether such molecules are immunologically active or inactive.

The EIA and RID tests are used in the same way to assay the filtered product. The EIA test results divided by the RID test results produce a second set of ratios representative of the relative concentrtion of each tested pathogen specific antibody to the total number of Ig molecules in the filtered product, whether such molecules are immunologically active or inactive. Comparison of each of the first set of ratios with each of the second set of ratios will indicate the percentage reduction in the relative concentration of each pathogen specific antibody and is representative of the percentage of Ig molecules which have been immunologically deactivated by the process of the present invention.

The combined EIA/RID test procedures described above threfore represent one technique for verifying that the immunological activity of the Ig molecules has been substantially maintained during implementation of the process of the present invention. A series of related combined test procedures can be applied to the initial and intermediate process steps and to the final product to identify and eliminate process conditions responsible for unacceptable reductions in the immunological activity of Ig molecules. Once the process has been stabilized, it may be possible to discontinue the combined EIA/RID test procedures until specific Ig immunological deactivation problems arise.

Once a complete set of process standards has been established, it may be possible to rely exclusively on the EIA test to monitor the distribution and concentration of pathogen specific antibodies in the filtered product. The concentration of a single pathogen specific antibody may be found to vary in direct proportion to the overall process-induced percentage reduction in Ig immunological activity. If so, that single pathogen specific antibody could be substituted for the combined EIA/RID tests to identify immunological deactivation problems.

Calves are commonly exposed to and require adequate passive immunity to the following pathogens:

1. *Escherichia coli*
2. *Salmonella dublin*
3. *CLostridium perfringens*, types B and C
4. *Clostridium chauvei*
5. *Haemopnilus somnus*
6. *Myxovirus parafluenza* 3
7. Infectious *Bovine Rhinotracheitis;* and
8. *Salmonella typhimurium*

EIA or equivalent test procedures will typically be configured to assay the presence and concentration of pathogen specific antibodies to this group of common pathogens. The scope of the assay techniques actually implemented in practicing the present invention on a commercial scale will depend on the complexity, repeatability and cost of the selected procedures as well as requirements for enhanced levels of passive immunity to specifically identified pathogens. For example, test procedures may be modified or expanded under certain conditions to determine the distribution and concentration of antibodies specific to pasteurela, clostridium perfringens, type D, Rota virus, Corona virus and others.

The specific asay techniques implemented in practicing the invention on a commercial scale will therefore typically be compatible with the group of pathogen specific antibodies incorporated in the specific quality control standard actually implemented to evaluate the acceptability of identified batchs of filtered product. The assay techniques may be modified as necessary to accommodate different quality control standards, for example regionalized quality control standards.

To use the filtered product to implement the last phase of the present invention and control the transfer of passive immunity to the newborn calf, a predetermined quantity of the filtered product is dissolved in a liquid such as colostrum, milk or water to produce a one or two liter Ig solution. This Ig solution is fed to the calf during the critical absorption period, generally within twelve hours and ideally within eight hours postpartum. Since a newborn calf typically consumes a maximum of only one to two liters of liquid during the initial suckling, it is desirable that the Ig concentration of the Ig solution is high enough to effect the transfer of an appropriate number of Ig molecules into the calf blood serum to achieve a minimum effective blood serum Ig concentration.

Market studies have indicated a user preference for administering medication to animals in dry form rather than in liquid form. In response to this expressed preference, the filtered product may be manufactured in pellet or capsule form. Packaging the filtered product in a two-section gelatinous capsule involves straight forward, existing technology and avoids exposing the filtered product to heat. After ingestion by the calf, the capsule dissolves and releases the filtered product. The filtered product subsequently dissolves in liquid such as water, milk or maternal colostrum consumed by the calf at the time of medication administration. The Ig from the resulting Ig solution is then absorbed through the calf's gut. Whether administered in dry or liquid form, the filtered product dosage remains the same.

To achieve calf blood serum Ig concentration levels of at least 15 mg/ml and preferably 20 mg/ml taught by the prior art as necessary to achieve an adequate transfer of passive immunity, a liquid Ig solution having a substantially higher Ig concentration must be ingested by a typical one hundred pound neonate calf. Since only about two hundred grams of the filtered product can be dissolved in one liter of colostrum, milk or water and since a neonate calf typically ingests only one to two liters of liquid per feeding, a filtered product having a forty to fifty percent Ig weight concentration should be capable of achieving a calf blood serum Ig concentration level recognized as acceptable by the prior art.

Referring again to FIG. 5, the flexibility of the present invention in controlling the distribution and concentration of pathogen specific antibodies in the filtered product will now be described in detail. FIG. 6A illustrates filtered product Sample 1 where the concentration of each antibody exceeds the designated grouping of minimum acceptable levels. FIG. 6B illustrates that Sample No. 2 is deficient in levels of antibody type numbers 4 and 5. FIG. 6C illustrates that filtered product Sample No. 3 is slightly deficient in levels of antibody types 3, 6 and 10. FIG. 6D illustrates the distribution of antibody type and concentration in a blended sample obtained by mixing equal weights of Samples 2 and 3. This blended sample includes an average concentration of each pathogen specific antibody which exceeds the designated quality control maximum levels. Thus, hen necessary, it may be advantageous to blend two or more different lots of dried immunologically active filtered product to produce a blended product meeting quality control standards which are not met by a single product lot.

By using more complex filtration procedures and ultrafiltration membranes capable of eliminating higher levels of non-Ig molecules, the ultrafiltration process is capable of producing an immunologically active filtered product which has an increased Ig concentration and hence an increased concentration of each pathogen specific antibody. In many cases, the resulting more concentratedd filtered product produced by higher levels of ultrafiltration may meet the designated quality control standards where the less concentrated filtered product failed to meet such standards.

Even without implementation of the blending techniques described above, the filtered product produced according to the process of the present invention tends to achieve a comparatively homogeneous distribution and concentration of pathogen specific antibodies since the milk processed into the whey Ig source material is typically drawn from a large, geographically distributed population of cows. While the milk produced by a single cow or by a small herd of cattle may lack necessary or desirable pathogen specific antibodies or may possess low Ig concentrations, the filtered product should not reflect the immunological inadequacies of such limited milk samples. On the contrary, due to its homogeneous nature, the filtered product will possess more uniformly useful immunological properties.

If a group of animals in one geographic location has been or is in danger of being exposed to an identifiable disease and if another group of animals in a different geographical location has already been exposed to such a disease and therefore possesses a high blood serum concentration of the necessary pathogen specific antibody, milk can be obtained from the exposed animals, processed into a filtered product having enhanced levels of the necessary pathogen specific antibody and fed to the newborn calves of unexposed dams. The immunity of those calves to the identified disease could thus be substantially enhanced.

Numerous other different techniques for exercising positive control ove the natural passive immunity transfer mechanism are available as a direct result of implementing the process of the present invention to produce a filtered product having a high concentration of immunologically active Ig molecules. Such additional techniques and resulting benefits would be obvious to a person of ordinary skill in the art in view of the teachings recited above.

When the process of the present invention is implemented in a selected manufacturing facility, the primary, intermediate and ultimate products should be assayed by means of the testing techniques described above to verify that Ig immunological activity has been substantially maintained. If at any step in the process the magnitude of the Ig immunological activity is significantly reduced or eliminated, the cause should be identified and corrected. Typically, reduction or elimination of Ig immunological activity is caused by excessive temperatures, exposure to a given temperature for an excessive time, excess microbial activity or molecular damage caused by excessive microbial enzyme activity.

Although other different processing methods and techniques are available for extracting and concentrating proteins from whey, most of these existing techniques are unsuitable for use in practicing the present invention since they deactivate Ig immunological activity, contaminate the Ig protein with undesirable chemical residues, or destroy the integrity of the Ig molecule by enzymatic or microbial action. Many of these existing whey protein concentration techniques are primarily intended for laboratory purposes and are incapable of producing commercial quantities of concentrated proteins.

The passive immunity transfer mechanism implemented according to the present invention has been discussed primarily in connection with dairy cattle. However, beef cattle and other non-bovine domestic animals that achieve passive immunity to disease in response to ingestion of a colostrum-like mammary gland secretion can also benefit from implementation of the process of the present invention. Dairy cattle have been focussed upon primarily due to the recognized and publicized immunity problems encountered and the resulting highly adverse economic impact on dairymen.

A recently published research study suggests the possibility that bovine antibodies such as the anti-rotavirus antibody may possess sufficient activity against human rotavirus strains to provide protection against symptomatic infection. If further investigation establishes that bovine antibodies do in fact combat selected human diseases, the immunologically active filtered product of the present invention could be used to provide protection against those diseases.

The results of the experiments involving the use of the whey-derived product described above will now be discussed in detail. The experimental test data summarized in Tables I-III has been simplified to eliminate what appeared to be inconsistent calf performance potentially attributable to physical and genetic differences in the neonate calves.

EXAMPLE 1

The inventive process described above was implemented by generally following the process steps depicted in FIG. 5. Clarified whey was directed to a single ultrafiltration module incorporating a single 100,000 Dalton ultrafiltration membrane. The ultrafiltration equipment and feedstock were maintained at ambient temperature during the filtration process. Repeated filtration with diafiltration was accomplished. The FIG. 5 process ultimately yielded dry, powdered filtered product having a seven percent Ig concentrated in an approximately eighty percent protein retentate.

Prior art research studies had indicated that the Ig content of colostrum and the quantity of colostrum consumed by a calf shortly postpartum must be sufficient to procure a calf blood serum Ig concentration of at least 15 mg/ml and preferably 20 mg/ml or higher. The seven percent Ig concentration of this filtered product and its maximum Ig concentration when dissolved in milk fell far short of the minimum Ig concentration taught by the prior art as necessary to achieve a transfer of passive immunity in a neonate calf. Nevertheless, this filtered product was tested on a group of dairy calves to investigate whether this whey-derived product had any potential for controlling or regulating the immune system of a neonate calf. The results of this first test of the filtered product are summarized in Table 1 below:

TABLE I

| CALF GROUP | 1. Ig SOURCE | 2. DOSAGE | 3. TOTAL Ig INGESTED PER DOSE | 4. TOTAL Ig INGESTED | 5. Ig CONCENTRATION IN LIQUID DOSE | 6. Ig CONCENTRATION IN ANIMAL BLOODSTREAM | 7. 30-DAY MORBIDITY SCORE | 8. LONG TERM HEALTH/ GROWTH RATE |
|---|---|---|---|---|---|---|---|---|
| 1. | Milk | 2 liters, 2 times | Near Zero | Near Zero | Near Zero | Near Zero | 25 | Much worse than Control Group |
| 2. | Colostrum | 2 liters, 2 times | 100–360 g | 200–720 g | 50–180 mg/ml | 17–35 mg/ml | 50 | Control Group |
| 3. | Product (600 g) | 2 liters, 2 times. 300 g Prod. per dose. | 21 g | 42 g | 10.5 mg/ml | 3–4 mg/ml | 80 | Better than Control Group |
| 4. | Product (200 g) | 2 liters 2 times 100 g Prod. per dose. | 7 g | 14 g | 3.5 mg/ml | 1–1.5 mg/ml | 58 | As good as Control Group |
| 5. | Product (100 g) | 2 liters, 1 time 100 g Prod. | 7 g | 7 g | 3.5 mg/ml | <1 mg/ml | 33 | Much worse than Control Group but better than Group 1 |

Thirty neonate calves were collected and divided into five groups of six calves each. Special arrangements were made to obtain these calves before they had an opportunity to suckle colostrum from their dams. The Group 1 calves were fed two liters of milk within about four hours postpartum and a second two liter feeding of milk approximately twelve hours after the first feeding. The Group 1 calves were deprived of Ig other than the insignificant levels of Ig normally found in whole milk.

The Group 2 calves served as a control group and received Ig via natural colostrum during their first two feedings postpartum. The timing of the two feedings was the same for all animals used in this initial test.

Calf Groups 3, 4 and 5 received whey-derived Ig was the filtered product produced through use of the 100,000 Dalton ultrafiltration membrane as described above. The Group 3 calves received two separate two liter feedings of milk. Three hundred grams of product was dissolved in each two liter feeding of milk such that each Group 3 calf received a total of six hundred grams of the filtered product. Since the seven percent Ig concentration of each three hundred gram dose of the product yielded a total of twenty-one grams of Ig per dose, each Group 3 calf received a total of forty-two grams of whey-derived Ig by consuming six hundred grams of the filtered product dissolved in milk.

Calf Group 4 received two two liter feedings of milk in which one hundred grams of filtered product had been dissolved. Each dose included a total of seven grams of Ig and the calf received a total of fourteen grams of whey-derived Ig.

Calf Group 5 received a single dose of one hundred grams of the filtered product dissolved in two liters of milk within about four hours postpartum. This group therefore received only seven grams of whey-derived Ig.

Blood samples were taken from each calf prior to its initial feeding, again twenty-four hours later, and at five, ten and twenty days postpartum. Each blood sample was assayed for total Ig content and for pathogen-specific antibody activity against six pathogens commonly occurring in calves. The total Ig content was determined by a Radial-Immune-Diffusion (R.I.D.) procedure against goat antibovine immunoglobulin. The enzyme-linked immunoassay (E.I.A.) procedure was used to determine pathogen-specific activity. Two determinations were made, one using goat antibovine immunoglobulin and one using a mouse antibovine immunoglobulin from a monoclonal hybridoma. Antigens for the pathogens tested came from commercial vaccines.

The calves acquired for this experiment were purchased at birth from eight different dairy farms. Eleven calves were obtained from one farm, eight from a second farm and the rest were distributed among the remaining six farms. To the maximum extent possible, all thirty calves used in this experiment received similar handling and treatment.

Four of the six Group 1 calves died within a few days after birth. The difference between the Group 1 milk-treated calves and the other calf groups which received either colostrum or the product was dramatic. The Group 1 calves were apparently not capable of controlling the transport of pathogenic organisms through the intestinal epithelium into systemic circulation. The Group 2-5 calves appeared to adequately limit this unwanted transport of pathogenic organisms.

The blood serum data indicated that two Group 1 calves had attained low Ig concentrations (0.3 and 2.3 mg/ml) prior to the first feeding. This Ig was apparently obtained via placental transfer or by undetected suckling of colostrum and was sufficient to protect these two animals from the transfer of pathogens during the first twenty-four hours of life while the epithelial cells were still capable of transferring ingesta into systemic circulation. In subsequent serum samples, these two resistent calves showed evidence of producing their own antibodies as indicated by increasing amounts of total serum Ig and by pathogenic-specific activity. The four Group 1 calves which died failed to show any evidence of increased antibody activity.

The Group 2 or control group calves were fed a maximum amount of high Ig concentration first milking colostrum having high levels of pathogen-specific antibodies of both polyclonal and monoclonal determination. Each calf received colostrum from a different cow, and in most cases, from a dairy other than the one where it was born. As expected, the resulting serum Ig concentration in all Group 2 calves at twenty-four hours post-feeding was very high (17-35 mg/ml.)

The Group 3 calves received a total of six hundred grams of the product which included forty-two grams of whey-derived Ig. These calves absorbed sufficient Ig to show a blood serum Ig level of 3-4 mg/ml and significant pathogen-specific antibody activity by twenty-four hours postpartum. The Group 3 calves experienced no mortality and only limited morbidity.

The Group 4 calves received two hundred grams of the filtered product containing fourteen grams of whey-derived Ig. These calves a attained blood serum Ig concentration of 1-1.5 mg/ml. In comparison to the Group 3 calves, the Group 4 calves had less pathogen-specific antibody activity at twenty-four hours postpartum, less active antibody and Ig production at twenty days postpartum and a higher level of mortality and morbidity. Two Group 4 calves died five days postpartum due to excessive diarrhea and dehydration.

The Group 5 calves received one hundred grams of the product containing seven grams of Ig. These calves were subject to high levels of morbidity and mortality. The amount of Ig received by these calves was sufficient to prevent septicemia or apparent absorption of ingested pathogenic microorganisms, but they were initially highly subject to diarrhea and subsequently to respiratory disease. Most of the Group 5 calves remained chronically morbid and two died at an early stage as a result of alimentary disease. One Group 5 calf attained a blood serum concentration of 1.2 mg/ml and showed significant pathogen-specific antibody activity from twenty-four hours postpartum through twenty days postpartum.

This initial experiment demonstrated that the well-being of a calf and its resistance to disease depended upon the absorption of a sufficient quantity of whey-derived Ig to achieve a blood serum concentration of at least one milligram per milliliter or better and the development of pathogen-specific antibodies at twenty-four hours postpartum. Any calves which did not meet these minimal requirements succumbed to disease and were generally chronically morbid.

All thirty of the calves involved in this initial experiment were carefully observed on a daily basis over the entire sixty day duration of the experiment. A combined subjective/objective morbidity score was maintained for each calf. As indicated by Column 7 of Table I, the Group 3 product-fed calf morbidity score of 80 substantially exceeded the Group 2 colostrum-fed calf morbidity score of 50. The morbidity scores of the milk-fed calves and of the Group 5 product fed calves fell substantially below the morbidity score of the Group 2 colostrum-fed calves.

Upon completion of this sixty-day experiment, calf mortality, morbidity and growth were carefully evaluated. The Column 8 entries in Table 1 indicate the relative, long term overall performance of each calf group. As indicated, the Group 3 calves which received forty-two grams of whey-derived Ig outperformed the Group 2 colostrum-fed calves. This result was surprising and totally unexpected in that the prior art uniformly taught that a sufficient amount of Ig must be consumed to achieve a calf blood serum Ig level of at least 15 mg/ml and preferably 20 mg/ml shortly postpartum to achieve adequate performance of a calf's immune system. In fact, the Group 2 colostrum-fed calves did achieve Ig blood serum levels of 17-35 mg/ml precisely as taught by the prior art and did achieve highly satisfactory immune system performance. Although the Group 3 product-fed calves achieved blood serum Ig levels of only 3-4 mg/ml, levels dramatically below the minimum acceptable levels taught by the prior art, the immune systems of these product-fed calves significantly outperformed the immune systems of the colostrum-fed calves.

In addition, the whey-derive Ig produced according to the process of the present invention satisfactorily accomplished each of the three separate immune system objectives known to be accomplished by natural colostrum. First, natural colostrum must function to prevent pathogenic organisms from entering the systemic circulation of the calf during the critical absorption period discussed above in connection with FIG. 2. During this critical absorption period, the neonate calf is capable of transferring Ig and other ingesta through the epithelial cells lining the intestinal wall into systemic circulation. As described above, only the Group 1 milk-fed calves showed symptoms and died of septicemia, indicating a total failure to achieve this first immune system performance objective. As indicated by the experimental test results tabulated in Table I, the whey-derived product, even at low Ig concentrations, was as effective as high Ig concentration natural colostrum in controlling pathogenic organism transfer via the small intestine during the critical absorption period. This experiment therefore confirmed that the whey-derived product did accomplish this first immune system performance objective.

The second immune system performance objective relates to the provision of an adequate level of Ig for intestinal absorption during the critical absorption period to provide effective passive immunity to the neonate until its active immunity becomes effective. The total quantity of whey-derived Ig fed to the Group 3-5 calves was only a fraction of the 200-720 gram Ig doses consumed by the Group 2 colostrum-fed calves. Nevertheless, the Group 3 calves which received only forty-two grams of Ig attained a blood serum Ig concentration of 3-4 mg/ml which resulted in an eight to tenfold increase in pathogen specific antibody activity in all six pathogens evaluted in this experiment. Furthermore, the Group 3 calves experienced a zero mortality rate and a morbidity score of eighty in comparison to the morbidity score of fifty of the Group 2 colostrum-fed calves. The Group 4 calves received only fourteen grams of whey-derived Ig yet experienced only two deaths and limited morbidity of the survivors—a level of immune system performance comparable to or better than the surviving Group 2 colostrum-fed calves.

The third immune system performance objective relates to the initiation of the calf's active immune system. As indicated by FIG. 7, a neonate calf relies on its Ig-derived passive immunity until its active immune system is activated and is able to produce an adequate, sustained level of antibody activity. Effective passive immunity enhances the ability of neonates to develop active immune responses thus affecting long term as well as short term health. If neonates consuming the whey-derived product did not achieve optimal active immune system function, the product could not function as a substitute for natural colostrum. The measurements made in connection with the Example 1 experiment clearly demonstrated that the four Group 1 calves which did not receive either placental or colostral Ig transfer did not show any increase in pathogen-specific activity from birth until death while both the colostrum-fed calves and the product-fed calves did initiate the active immune system.

The Example 1 experiment demonstrates that the Group 3 calves which received forty-two grams of the whey-derived Ig achieved overall immune system performance superior to that achieved by the Group 2 calves which received two maximum volume doses of high Ig concentration natural colostrum. The concentration of the six measured pathogens in the colostrum-fed calves substantially exceeded corresponding concentrations in any of the product-fed calves. The superior immune system performance of the Group 3 product-fed calves therefore tends to suggest that the whey-derived product contained antibodies for a much greater number of pathogens than were present in the colostrum taken from individual cows. The fact that the whey-derived Ig was derived from pooled milk representing literally hundreds of cows could readily explain the presence of a substantially broader spectrum of antibodies in the whey-derived product than with natural colostrum. This potential for securing broad spectrum immunity from whey-derived product represents a substantial advantage of the product over natural colostrum and provides a method for regulating both the level of activity of a calf's immune system as well as a method for controlling the spectrum of pathogens which can be effectively neutralized by a calf's immune system.

The Example 1 experiment therefore establishes that the whey-derived product is capable of functioning as a fully acceptable substitute for natural colostrum (1) by preventing pathogenic organisms from entering systemic circulation during the neonatal stage, (2) by transferring effective passive immunity comparable to or better than natural colostrum and (3) by providing factors which initiate and enhance broad spectrum active immunity at an early stage.

EXAMPLE 2

The whey-derived filtered product was tested a second time with five separate groups of ten calves each as indicated by Table II below. A 120,000 Dalton spiral ultrafiltration membrane and a 100,000 Dalton hollow fiber ultrafiltration membrane were used independently to produce separate batches of filtered product having a nine percent Ig concentration. Techniques essentially identical to those used in connection with Example 1 were utilized to produce these two batches of filtered product. The Group 1 colostrum-fed calves were used as a control group in a manner similar to that discussed in connection with the Group 2 calves of Example 1. The feedings of all calves in the Example 2 experiment were accomplished within four hours postpartum and again twelve hours later. The Table II results represent informal conclusions based on preliminary data subject to further analysis and modification. This test was conducted under highly severe weather conditions with calf exposure to an unusually broad spectrum of pathogens.

TABLE II

| CALF GROUP | 1. Ig SOURCE | 2. DOSAGE | 3. TOTAL Ig INGESTED PER DOSE | 4. TOTAL Ig INGESTED | 5. Ig CONCENTRATION IN LIQUID DOSE | 6. LONG TERM HEALTH |
|---|---|---|---|---|---|---|
| 1. | Colostrum | 2 liters, | 100-360 g | 200-720 g | 50-180 mg/ml | Control Group |

TABLE II-continued

| CALF GROUP | 1. Ig SOURCE | 2. DOSAGE | 3. TOTAL Ig INGESTED PER DOSE | 4. TOTAL Ig INGESTED | 5. Ig CONCENTRATION IN LIQUID DOSE | 6. LONG TERM HEALTH |
|---|---|---|---|---|---|---|
| 2. | Product (Spiral 300 g) | 2 times 2 liters, 2 times 150 g Prod. per dose | 13.5 g | 27 g | 6.75 mg/ml | Much worse than Control Group |
| 3. | Product (Spiral 300 g) | 1 liter, 1 time 300 g Prod. 2 liter, 1 time colostrum | 27 g via Product Plus Colostrum | 27 g via Product Plus Colostrum | 13.5 mg/ml | Worse than Control Group |
| 4. | Product (Spiral 600 g) | 2 liters, 2 times 300 g Prod. per dose | 27 g | 54 g | 13.5 mg/ml | As good as Control Group |
| 5. | Product (Hollow Fiber 600 g) | 2 liters, 2 times 300 g Prod. per dose | 27 g | 54 g | 13.5 mg/ml | As good as or better than Control Group |

The Group 2 calves were administered two one hundred fifty gram doses of the product dissolved in the milk for a total transfer of twenty-seven grams of whey-derived Ig. As indicated by Column 6 of Table II, the Group 2 calf immune system performance was much worse than that of the Group 1 control group.

Within four hours postpartum, the Group 3 calves were administered three hundred grams of the product dissolved in milk for a total transfer of twenty-seven grams of whey-derived Ig. The second feeding took the form of a two liter dose of natural colostrum including between two hundred to seven hundred and twenty grams of colostrum-derived Ig. The immune system of the Group 3 calves responded well during the early stages of this experiment, but ultimately produced calves having long term health worse than that of the control group.

The Group 4 calves were administered two three hundred gram doses of the product dissolved in milk for a total transfer of fifty-four grams of whey-derived Ig. The immune system of the Group 4 calves performed very well and produced calves having long term health as good as that of the control group.

The Group 5 calves were administered two three hundred gram doses of the product dissolved in milk for a total transfer of fifty-four grams of whey-derived Ig. The immune system of the Group 5 calves performed very well and produced calves having long term health as good as or better than that of the control group.

The results of this second experiment parallel the results of the first experiment. The Table II data indicates that under extremely severe conditions, fifty-four grams of whey-derived Ig is capable of producing a highly satisfactory immune system performance. The superior immune system performance achieved by the Group 4 and 5 calves which received fifty-four grams of whey-derived Ig is consistent with the superior immune system performance achieved by the Group 3 calves of the first experiment which received forty-two grams of whey-derived Ig.

The inferior immune system performance achieved by the Group 2 calves indicates that the administration of only 13.5 grams of whey-derived Ig at each of the two initial feedings did not achieve a performance level which would render this Ig dosage acceptable as a substitute for natural colostrum. Although the immune system of the Group 3 calves that received twenty-seven grams of the product followed by colostrum performed worse than the control group under the severe conditions of this test, such performance indicates that a twenty-seven gram dosage may be adequate under more normal conditions.

EXAMPLE 3

The whey-derived product of the present invention was tested a third time at a second facility separate from the one used to accomplish the Example 1 and Example 2 experiments. This third test involved a total of sixty calves from a single herd which were divided into three groups of twenty calves each. This test was conducted under highly favorable test conditions.

Two different concentrations of Ig were used in implementing this third experiment. A 100,000 Dalton hollow fiber ultrafiltration membrane was used to produce a product having a nine percent Ig concentration. The same 100,000 Dalton hollow fiber ultrafiltration membrane was also used to produce a product having a twelve percent Ig concentration. Calves were fed either three hundred grams of the nine percent Ig concentration product or two hundred twenty-seven grams of the twelve percent Ig concentration product dissolved in one liter of milk in order to transfer a total of twenty-seven grams of whey-derived Ig via a single dose. The results of this experiment are tabulated in Table III below. This table incorporates informal conclusions based on preliminary data subject to further analysis and modification:

TABLE III

| CALF GROUP | 1. IG SOURCE | 2. DOSAGE | 3. TOTAL Ig INGESTED VIA PRODUCT | 4. LONG TERM HEALTH |
|---|---|---|---|---|
| 1. | Colostrum | 5 × 1 liter feedings through day four | — | Control Group |

TABLE III-continued

| CALF GROUP | 1. IG SOURCE | 2. DOSAGE | 3. TOTAL Ig INGESTED VIA PRODUCT | 4. LONG TERM HEALTH |
|---|---|---|---|---|
| 2. | Product | 1 liter, 1 time 300 g 9% Ig Product or 227 g 12% Ig Product | 27 g | As good as Control Group |
| 3. | Product followed by Colostrum | 1 liter Product 1 time (300 g 9% or 227 g 12%) Then 4 × 1 liter feedings of colostrum through day four | 27 g | As good as Control Group |

The Group 1 calves received five separate one liter feedings of natural colostrum through the fourth day postpartum. This group served as the control group. The Group 2 calves received twenty-seven grams of whey-derived Ig dissolved in one liter of milk. Column 4 of Table 3 indicates that the immune system of the Group 2 calves functioned to achieve long term health as good as that of the control group.

The Group 3 calves received twenty-seven grams of whey-derived Ig dissolved in one liter of milk at the initial postpartum feeding. This group then received four additional one liter feedings of natural colostrum through the fourth day postpartum. The immune system of the Group 3 calves functioned to achieve long term health as good as that of the control group.

This third experiment indicated that if twenty-seven grams of the whey-derived Ig product are administered shortly postpartum, an immune system performance comparable to that attainable by natural colostrum may be achieved under good conditions. This result when correlated with the result achieved by the Group 2 calves in this Example 2 experiment indicates that under good conditions twenty-seven grams of whey-derived Ig represents an adequate dosage of Ig to achieve each of the three objectives achieved by natural colostrum. This is consistent with the results obtained by the Group 3 calves in the Example 2 experiment and indicates that a second feeding dose of natural colostrum may not be essential to achieve an adequate level of immune system performance. The fact that the Group 4 calves in the Example 1 experiment received only fourteen grams of whey-derived Ig and that this level of Ig did not achieve immune system performance comparable to that attainable through use of natural colostrum tends to indicate that whey-derived Ig produced according to the process of the present invention should be administered at a level in excess of fourteen grams. A minimum level of whey-derived Ig slightly below twenty-seven grams therefore appears capable of achieving immune system performance comparable to that attainable through use of natural colostrum under good conditions. To achieve immune system performance equal to or better than that available from use of high quality natural colostrum, approximately 40-50 grams of Ig should be ingested by the neonate during the first twenty-four hours postpartum.

The fact that the experimental results discussed above indicate that both forty-two grams and fifty-four grams of whey-derived Ig achieved immune system performance superior to that achieved by calves receiving from two hundred to seven hundred and twenty grams of colostrum-derived Ig tends to indicate the possible existence of an optimum level of Ig transfer to a neonate which is capable of achieving a higher level of immune system performance than would be possible by transferring a quantity of Ig in excess of this optimum level. This potential correlation between an optimum Ig dosage and peak immune system performance has not been confirmed nor has a specific upper limit been defined for a maximum desirable level of Ig transfer to a neonate calf.

Although the experimental test results recited in Tables I, II and III have expressed the quantity of Ig ingested by a calf in terms of grams, the ratio of the weight of the whey-derived Ig to animal weight is the appropriate parameter to evaluate in determining an appropriate dosage of the product for any particular animal. Since substantially all of the animals used in the various experiments described above weighed from between ninety to one hundred pounds, animal weight was not a significant variable and was disregarded in tabulating these results.

If the experimental results are evaluated as indicating that a minimum of twenty-five grams or an optimum level of forty to fifty grams of whey-derived Ig should be administered to a calf having a weight of one hundred pounds, these results indicate that at least a minimum 0.055 and preferably 0.09-0.10 percent ratio of whey-derived Ig to animal weight should be administered to any neonate calf. Applying this ratio to a neonate calf having a body weight of one hundred and twenty-five pounds (56,750 grams) indicates that a minimum of appropriately thirty-one grams of whey-derived Ig should be administered to that calf in a single dose given within four hours postpartum. Various other product dosage levels, dosage distributions and dosage combinations with natural colostrum would be readily apparent to one of ordinary skill in the art in view of the detailed experimental results tabulated above. In addition, it is clear that the whey-derived product could readily function as a supplement for natural colostrum to either boost the effective level of Ig in natural colostrum having an insufficient level of Ig or to serve as a source of broad spectrum active immunity ultimately achieved by the immune system of a calf or other bovine. The whey-derived product could also be used on a continuous basis as a food supplement for a calf, a mature cow or any other animal to enable the immunolically active immunoglobulin molecules in the product to attack pathogens present in the digestive system of the animal. Comparatively low levels of the product could be used when it functions as a food supplement, potentially on the order of approximately two grams or less per day per hundred pounds of animal weight.

To test this hypothesis, a forty animal sixty day test was accomplished. Twenty four hundred pound intermediate maturity calves served as a control group and received normal high protein feed rations. The remaining twenty four hundred pound intermediate maturity calves consumed normal high protein feed rations plus a supplement of approximately five to ten grams per day of filtered product having a seven percent Ig concentration.

During the first thirty days of this test, the daily weight gain of the product-fed calves exceeded the control group daily weight gain by 0.4 pounds—a sixteen percent higher average daily weight gain. During the second thirty days of the test, the daily weight gain of the product-fed calves exceeded the control group daily weight gain by 0.3 pounds per day. In general, the product-fed calves appeared healthier and experienced a higher growth rate and lower morbidity than the control group calves. This test appeared to prove the utility of the whey-derived product as a feed supplement for either growing or mature animals.

A quantity of whey-derived filtered product was produced using an ultrafiltration system including a 100,000 Dalton hollow fiber ultrafiltration membrane. Recirculation and diafiltration techniques were used in an attempt to obtain a maximum Ig concentration. This experiment ultimately yielded a filtered product having a twelve percent Ig concentration.

Of the six percent solids in raw whey, approximately eighty percent of these solids represent lactose, another ten percent represent minerals and the remaining ten percent represent proteins. As indicated by FIG. 11, approximately seven to ten percent of this whey protein fraction represents Ig proteins. Whenever the Ig concentration in the dry, filtered product exceeds this seven to ten percent Ig concentration in whey, a certain portion of the lower molecular weight proteins must be removed from this whey protein fraction by ultrafiltration to achieve this enhanced Ig concentration. This twelve percent Ig concentration obtained as described above therefore resulted from the elimination of a certain percentage of the lower molecular weight proteins from the ultrafiltration retentate.

Two hundred twenty-seven gram doses of product having a twelve percent Ig concentration were used in experiments conducted at the two test sites. When two hundred twenty-seven grams of this twelve percent Ig were dissolved in one liter of milk, a total of twenty-seven grams of whey-derived Ig could be transferred to a calf in a single feeding. At one test site, the immune system performance of calves receiving the twelve percent Ig product was as good as that of the colostrum-fed control group. At the other test site where the calves were stressed by environmental and other conditions to a higher degree than that experienced at the first test site, the immune system performance of the calves administered the twelve percent Ig product was not as good as that of the colostrum-fed control group. These calves experienced morbidity at a higher level than the colostrum-fed control group. At the better performing test site, the calves receiving the twelve percent Ig product were administered one dose including twenty-seven grams of whey-derived Ig followed by four more feedings of clostrum while the calves at the other more stressful test site received only a single twenty-seven gram dose of the twelve percent Ig product.

The experimental anomaly described above indicates the possibility that elimination of lower molecular weight proteins to achieve high product Ig concentrations may have a significant, adverse effect on the performance of the whey-derived product as a colostrum substitute.

Referring now to FIG. 8, an ultrafiltration system slightly modified from that depicted in FIG. 5 will be described in detail. The whey, fat and casein feedstock is clarified in a standard item of cheese processing equipment to produce a fat and casein byproduct and a clarified whey source material used in practicing the present invention. The clarified whey is then directed through pasteurization equipment to accomplish a second flash pasteurization which destroys unwanted bacteria remaining in the whey as a result of the utilization of lactobacillus bacteria and rennet as agents in the cheese manufacturing process. This second short duration flash pasteurization has been implemented and found to have no adverse effects on the immunological activity of the Ig molecules in the clarified whey.

The pasteurized whey is then directed to ultrafiltration equipment which incorporates one or more ultrafiltration membranes having permeability levels of from 1,000 to 10,000 Daltons. Experience with the 100,000 Dalton ultrafiltration membrane described in connection with FIG. 5 above has indicated that a gel rapidly forms on the ultrafiltration membrane substantially reducing its permeability to a level well below 100,000 Daltons. An ultrafiltration membrane having a permeability of from 1,000 to 10,000 Daltons adequately eliminates the unwanted water, lactose and minerals from the whey. The residual level of lactose and minerals in the ultrafiltration retentate does not produce unwanted side effects when the whey retentate is dried and administered to neonate calves.

The ultrafiltration permeate is directed to a waste disposal unit. The ultrafiltration retentate includes approximately eighty percent protein material having an Ig concentration on the order of eight percent. This retentate is directed to a spray dryer which yields a dry, filtered product having approximately an eight percent Ig concentration which has been tested and proven to have substantial immunological activity. This whey-derived filtered product is then packaged and stored and is ultimately dissolved in a liquid such as milk or water and fed to a neonate during the critical absorption period as was the case in connection with the analogous material described with FIG. 5 above. This whey-derived Ig will possess a broad spectrum of antibodies since it is derived from the whey by-product of milk obtained from hundreds of cows in geographically distributed, separate herds.

The ultrafiltration processes described in connection with FIGS. 5 and 8 are capable of producing a colostrum substitute filtered product which can be manufactured and sold at a profit. However, to enhance the profitability of the product incorporating whey-derived Ig, it is desirable to reduce the size of the dose to a level substantially below the six hundred gram dosage level administered to the Example 1 Group 3 calves. Since about eighty percent of the dry filtered product obtained from the ultrafiltration process represents proteins which have a high economic value as a food product, it would substantially enhance the economic attractiveness of the process if some non-Ig protein components in the dry filtered product could be eliminated from the product to increase the Ig concentration in the product. If this could be accomplished, such non-Ig proteins could be sold as a food product through existing commercial channels and could thereby reduce the net cost of manufacturing the product administered to neonate calves in practicing the present invention.

Referring now to FIGS. 8, 9 and 10, the output of an ultrafiltration system can be combined with an ultrafiltration/ion exchange system to produce a blended product having a substantially enhanced Ig concentration without a significant reduction in the concentration of smaller molecular weight proteins. With such an ehanced Ig concentration in the blended product, an adequate level of whey-derived Ig can be transferred in a significantly reduced product dose size resulting in a substantial cost savings by avoiding the use of a significant percentage of the non-immunologifally active protein material.

In implementing this different technique for producing a colostrum substitute product, the FIG. 8 ultrafiltration process is utilized to produce a filtered product having approximately an eight percent Ig concentration. As indicated in FIG. 10, this Stream A eight percent Ig product is blended with a stream B ion exchange product having a fifty percent Ig concentration to achieve a significantly higher Ig concentration whey-derived Ig product.

Referring now to FIG. 9, the Stream B combined ultrafiltration/ion exchange process for producing a fifty percent Ig concentration product will now be described in detail. The FIG. 9 process utilizes the same whey, fat and casein feedstock as that used in the FIG. 8 ultrafiltration system. The ion exchange Ig separation as depicted in FIG. 9 may either be accomplished at the same site where the FIG. 8 ultrafiltration system is located or more typically will be performed at a different cheese processing plant.

The feedstock is clarified to remove fat and casein and the clarified whey process source material is directed through a second flash pasteurization step as was the case with the FIG. 8 ultrafiltration system.

Ultrafiltration of the clarified whey is accomplished with an ultrafiltration unit having a 1,000 to 10,000 Dalton ultrafiltration membrane to produce a thirty-seven percent retentate. The ultrafiltration permeate is directed to a waste disposal unit. Diafiltration may be used with this ultrafiltration process to remove salts from the ultrafiltration retentate such that its conductivity is reduced to a near zero level on the order of 2-3 mMhos. Above such conductivity levels, ion exchange equipment is rendered ineffective. Alternative techniques such as electrodialysis may be used to desalinize the retentate.

The thirty-seven percent protein retentate is then directed to an ion exchange unit of a type well known to those of ordinary skill in the appropriate field. Such an ion exchange unit can be configured to function in either a cation or anion extraction mode. At present, the cation mode is preferred primarily for economic reasons.

The ion exchange unit operates on the whey protein ultrafiltration retentate to separate out Ig proteins possessing a charge different from most non-Ig proteins. When operated as a cation ion exchange system at a pH somewhat lower than the normal 6.2 pH of whey, the bed of the ion exchange unit collects Ig proteins and other proteins at a ratio of approximately fifty percent Ig proteins to fifty percent other proteins. When the bed of the ion exchange unit is eluted, an ion exchange product having about a fifty percent Ig concentration and a fifty percent non-Ig protein concentration is obtained.

When the ion exchange unit is operated in the anion mode at the normal 6.2 pH of whey, the non-Ig proteins bind to the ion exchange bed while the oppositely charged Ig proteins pass through without binding. The anion process also produces about a fifty percent Ig concentration product.

Specific configurations of both cation and anion ion exchange units are recited in Examples 4 and 5 below:

EXAMPLE 4

Ig is purified by a cation exchange using a cation exchange material such as S-Sepharose (Pharmacia) equilibrated with 10 mM acetate, pH 4.5–6.0, e.g. 5.0. A desalted solution of whey proteins with a conductivity of 2 mMhos (2mS) is adjusted to pH 5.0 and exposed to the S-Sepharos gel at about 2–500 mg/ml of gel, for example 4 ml whey protein solution at 50 mg/ml mixed with 2 ml gel or passed through a column of 2 ml gel. About fifty percent or more of the Ig in the whey protein solution binds to the gel. Unbound proteins are washed away with 10 mM acetate, pH 5.0 or with water (5 ml for 2 ml gel). Ig is released and obtained by exposing the gel to high salt (100 mM NaCl in 10 mM acetate) or high pH ($\geq 8.0$), for example 100 mM dibasic phosphate or ammonium carbonate. Five milliliters eluting buffer is adequate for 2 ml gel.

EXAMPLE 5

Anion exchange is used to purify Ig by binding non-Ig proteins. Anion exchange gel such as Q-sepharose or Amicon-AM gel is equilibrated with 10 mM phosphate at pH 7.5. A low salt (2mS) solution of whey proteins is adjusted to pH 7.5 and mixed with anion exchange gel (100 mg protein per ml gel). Unbound protein is collected and is Ig rich (80% or more of the protein is Ig).

Referring now to FIG. 10, the eight percent Ig product obtained via the FIG. 8 process Stream A is blended with fifty percent Ig concentration ion exchange product produced by the FIG. 9 Stream B ion exchange Ig separation process. When the Stream A eight percent product is blended in an appropriate ratio with the Stream B fifty percent Ig concentration product, a product having a controllable Ig concentration of between eight percent to fifty percent Ig may be obtained.

Present economic considerations suggest the desirability of using a product dose of no more than three hundred grams to minimize the cost of the non-Ig protein components.

The experimental test results tabulated above indicate that a high level of immune system performance will be achieved with a single dose of the product containing about forty grams of immunologically active, whey-derived Ig. If two hundred and thirty-eight grams of the Stream A eight percent concentration Ig product ($8\% \times 238$ g = 19 g Ig) is blended with forty-two grams of fifty percent concentration Ig from Stream B ($50\% \times 42$ g = 21 g Ig), a two hundred and eighty gram dose is produced having forty grams of whey-derived Ig. Forty grams of Ig in a total dose size of two hundred eighty grams represents a fourteen percent Ig concentration.

Since the Stream A ultrafiltration product was filtered only to an eight percent Ig concentration, essentially none of the non-Ig proteins were eliminated from this two hundred thirty-eight gram component of the overall two hundred eighty gram dose. Since the Stream A ultrafiltration retentate was only processed to a maximum protein concentration of eighty percent protein, approximately twenty percent of the retentate will comprise lactose and minerals. Experimental testing has indicated that this comparatively small level of lactose and minerals does not adversely affect neonate calves and will not cause unwanted scours.

As indicated by FIG. 9, the residual product obtained from the second output of the ion exchange unit comprises approximately thirty-five percent protein. This specific percent concentration protein has been selected since this is the standard, commercially acceptable protein concentration for use in the food product market. This thirty-five percent protein product is passed through an evaporator and spray dryer and is ultimately packaged for resale in the existing protein food product market.

The sale of this non-immunologically active protein product provides a substantial process cost recovery and significantly reduces the net cost of the blended, highly concentrated Ig product achieved by combining the Stream A low concentration Ig product with the Stream B high Ig concentration product.

The blended whey-derived product is packaged and marketed. To administer this packaged product to a neonate calf, the package is emptied into an appropriate one or two liter quantity of milk, dissolved and fed to the neonate as described above.

Based on the experimental test results tabulated above, the blended product should contain at least about twenty-five grams of Ig for use as a colostrum substitute with a typical one hundred pound neonate calf under good conditions. The 0.055 percent ratio of Ig weight to animal body weight should be observed for neonate animals having weights differing from the one hundred pound typical neonate calf weight. To achieve immune system performance equal to or better than high quality natural colostrum, approximately forty to fifty grams of Ig should be ingested by the neonate during the first twenty-four hours postpartum (0.09%–0.10%).

As was the case with the straight ultrafiltration product, the blended Ig product may also be used as a colostrum supplement rather than as a colostrum substitute. In addition, the blended product may be used as an immunologically active food supplement. Although a specific ratio of Stream A product to Stream B product was described above, it would be readily apparent based upon the detailed description above that various other ratios of Stream A to Stream B could be blended together to achieve differing levels of Ig in the blended product. The specific application of the blended Ig product as well as various economic and cost factors would dictate the specific quantity of Stream A which is blended with Stream B.

It will be apparent to those skilled in the art that the disclosed product and process for controlling the natural passive immunity transfer mechanism of domestic animals may be modified in numerous ways and may assume many embodiments other than the preferred forms specifically set out and described above. Accordingly, it is intended by the appended claims to cover all such modifications of the invention which fall within the true spirit and scope of the invention.

I claim:

1. A process for transferring passive immunity to a neonate domestic animal during a critical absorption period and for enhancing the initiation of active immunity in said animal comprising the steps of:
   a. providing whey derived from ordinary milk, said whey having a measurable but low level concentration of immunologically acitve immunoglobulin;
   b. ultrafiltering said whey through ultrafiltration means having an ultrafiltration membrane permeable to low molecular weight materials including lactose and minerals and with a mean pore size of less than one hundred and sixty thousand Daltons until reaching a retentate protein concentration of at least about a 70% weight concentration to yield a retenate having a substantially decreased concentration of lactose and minerals, said ultrafiltering step being accomplished under thermal conditions which substantially preserve the EIA titer of the immunoglobulin in the whey;
   c. drying said retentate under thermal conditions which substantially preserve the EIA titer of the immunoglobulin in said retentate to produce a filtered product having at least about a seven percent weight concentration of immunologically active immunoglobulin; and
   d. feeding a predetermined quantity of said filtered product to said animal during the critical absorption period such that the weight of the immunoglobulin in the predetermined quantity of said filtered product is equal to or greater than about 0.055 percent of the weight of said animal and the animal blood serum immunoglobulin concentration is elevated to a level of at least about 1 mg/ml in response to ingestion of the predetermined quantity of said filtered product.

2. The process of claim 1 wherein the ultrafiltration membrane mean pore size is greater than about one thousand Daltons.

3. The process of claim 2 wherein the ultrafiltration membrane mean pore size is greater than about ten thousand Daltons.

4. The process of claim 3 wherein the ultrafiltration membrane mean pore size is greater than about one hundred thousand Daltons.

5. The process of claim 2 where the formation of a gel layer on said ultrafiltration membrane reduces the effective mean pore size to a level well below one hundred and sixty thousand Daltons.

6. The process of claim 1 wherein the ultrafiltering step is accomplished within a first ultrafiltration unit to produce a first ultrafiltration retentate.

7. The process of claim 6 wherein said first ultrafiltration retentate is directed to a second ultrafiltration unit and wherein said ultrafiltering step is continued to produce a second ultrafiltration retentate.

8. The process of claim 7 wherein said first ultrafiltration unit includes a first ultrafiltration membrane having a mean pore size of more than about ten thousand Daltons and less than about one hundred and sixty thousand Daltons and wherein said second ultrafiltration unit includes a second ultrafiltration membrane having a mean pore size selected to retain substantially all immunoglobulin proteins while passing at least some other lower molecular weight components of the first stage ultrafiltration retentate to thereby further increase the concentration of immunologically active immunoglobulin in the second stage ultrafiltration retentate.

9. The process of claim 2 wherein the predetermined quantity of said filtered product fed to said animal includes a 0.09% ratio of immunoglobulin to animal weight.

10. The process of claim 2 wherein said ultrafiltering step is continued until the retentate protein concentration reaches at least about an 80% weight concentration.

11. The process of claim 2 wherein the feeding step is commenced within twenty-four hours postpartum.

12. The process of claim 11 wherein the feeding step is commenced within twelve hours postpartum.

13. The process of claim 12 wherein the feeding step is commenced within eight hours postpartum.

14. The process of claim 11 wherein said animal includes a calf.

15. The process of claim 2 wherein said animal is a calf and wherein at least about twenty-five grams of immunologically active immunoglobulin is fed to said calf in no more than about six hundred grams of said filtered product for each one hundred pounds of animal body weight.

16. The process of claim 15 wherein at least about twenty-five grams of immunologically active immunoglobulin is fed to said calf in no more than about four hundred grams of said filtered product for each one hundred pounds of animal body weight.

17. The process of claim 15 wherein at least about twenty-five grams of immunologically active immunoglobulin is fed to said calf in no more than about three hundred grams of said filtered product for each one hundred pounds of animal body weight.

18. The process of claim 15 wherein said filtered product is dissolved in a liquid prior to said feeding step.

19. The process of claim 18 wherein said liquid includes milk.

20. The process of claim 2 wherein the predetermined quantity of said filtered product is fed to said animal in a single dose dissolved in liquid within twelve hours postpartum and wherein the weight of the immunoglobulin in said filtered product dose is equal to or greater than about 0.09% of the weight of said animal.

21. The process of claim 5 wherein the predetermined quantity of said filtered product is fed to said animal in a single dose dissolved in liquid within twelve hours postpartum.

22. The process of claim 1 including the further steps of:
   a. ultrafiltering said whey through a second process stream including ultrafiltration means having an ultrafiltration membrane permeable to low molecular weight materials including lactose and minerals and with a mean pore size of less than one hundred and sixty thousand Daltons until reaching a retentate protein concentration of at least about seventy percent weight concentration to yield a retentate having a substantially decreased concentration of lactose and minerals, said ultrafiltering step being accomplished under conditions which substantially preserve the EIA titer of the immunoglobulin in the whey;
   b. desalinizing said ultrafiltration retentate until the electrical conductivity of said retentate is not substantially above zero;
   c. passing said desalinized retentate through an ion exchange unit to produce an ion exchange product having a concentration of immunologically active immunoglobulin greater than twenty percent;
   d. blending said filtered product of claim 25 step "c" with said ion exchange product to produce a blended product having a concentration of immunologically active immunoglobulin greater than that of said filtered product and less than that of said ion exchange product; and
   e. feeding a predetermined quantity of said blended product to said animal during the critical absorption period such that the weight of immunoglobulin in said blended product consumed by said animal is equal to or greater than 0.055 percent of the weight of said animal and the animal blood serum immunoglobulin concentration is elevated to a level of at least about 1 mg/ml in response to ingestion of the predetermined quantity of said blended product.

23. The process of claim 22 wherein a diafiltration process is used to desalinize said ultrafiltration retentate.

24. The process of claim 23 wherein said diafiltration process is continued until the electrical conductivity of said ultrafiltration retentate is equal to or less than about three mMhos.

25. The process of claim 22 wherein the concentration of immunoglobulin in said second stream ultrafiltration retentate is equal to or less than about ten percent.

26. The process of claim 22 wherein said animal is a calf.

27. The process of claim 1 wherein the animal blood serum immunoglobulin concentration is elevated to a level of less than about 15 mg/ml in response to ingestion of the predetermined quantity of said filtered product.

28. A process for enhancing the health and growth rate of a domestic animal comprising the steps of:
   a. providing whey derived from ordinary milk, said whey having a measurable but low level concentration of immunologically active immunoglobulin having various different pathogen specific antibodies;
   b. ultrafiltering said whey through ultrafiltration means having an ultrafiltration membrane permeable to low molecular weight materials including lactose and minerals and with a mean pore size of less than one hundred and sixty thousand Daltons until reaching a retentate protein concentration of at least aout a 70% weight concentration to yield a retentate having a substantially decreased concentration of lactose and minerals, said ultrafiltering step being accomplished under thermal conditions which substantially preserve the immunological activity of the immunoglobulin in the whey;
   c. drying said retentate under conditions which substantially preserve the immunological activity of the immunoglobulin in said retentate to produce a filtered product having at least about a seven percent weight concentration of immunologically active immunoglobulin;
   d. assaying said filtered product to measure the distribution and concentration of selected pathogen specific antibodies in said immunoglobulin to determine quantified antibody activity levels for said filtered product;
   e. comparing said quantified antibody activity levels with a quality control standard to verify that the immunological activity of said antibodies in said filtered product has been substantially preserved; and
   f. combining said assayed filtered product with feed consumed by said animal such that the weight of the immunoglobulin in said filtered product consumed daily by said animal is equal or greater than about $1.9 \times 10^{-4}$ percent of the weight of said animal.

29. The process of claim 28 wherein the weight of the immunoglobulin in said assayed filtered product consumed daily by said animal is equal to or greater than about $3 \times 10^{-4}$ percent of the weight of said animal.

30. The process of claim 28 including the further step of rejecting said assayed filtered product if the quantified activity levels of said antibodies do not equal or exceed the quality control standard.

31. The process of claim 28 wherein an E.I.A. assay is used to assay the distribution and concentration of selected pathogen specific antibodies in said filtered product.

32. The process of claim 28 wherein a radial immune diffusion test is used to assay the weight concentration of immunoglobulin in said filtered product.

33. The process of claim 31 wherein a radial immune diffusion test is used to assay the weight concentration of immunoglobulin in said filtered product.

* * * * *

UNITED STATES PATENT AND TRADEMARK OFFICE
CERTIFICATE OF CORRECTION

PATENT NO. : 4,816,252
DATED : March 28, 1989
INVENTOR(S) : Dr. Gerald H. Stott, Dr. David O. Lucas It is certified that error appears in the above-identified patent and that said Letters Patent is hereby corrected as shown below:

Column 1, line 28, "As illustrated by FIG. 1" should be deleted.

Column 1, line 29, "this" should be deleted and --This-- should be substituted.

Figures 2, 3:
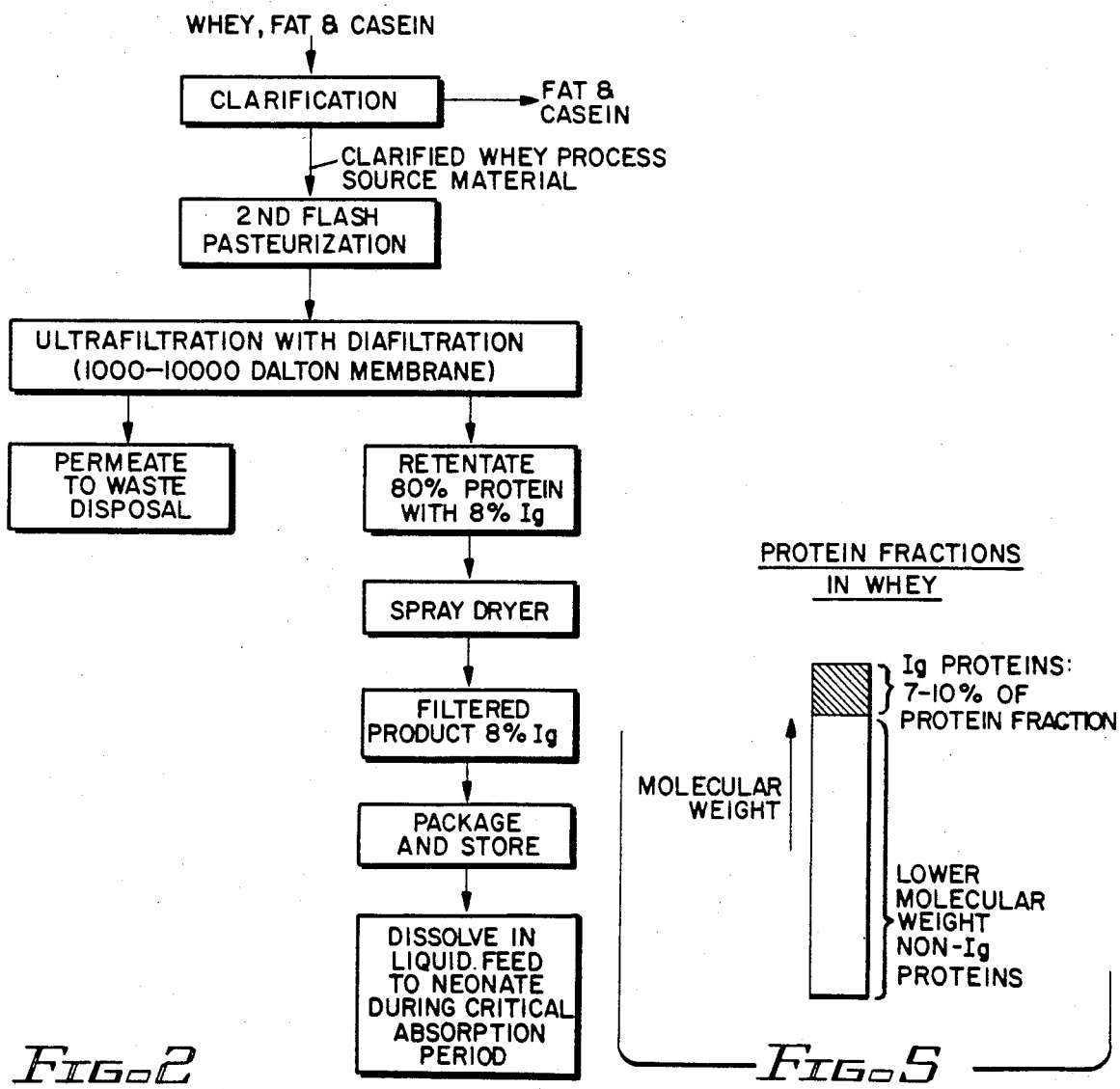
FIG. 2 is a graph illustrating the bovine gut closure phenomenon where the ability of the gut to absorb large Ig molecules rapidly diminishes after birth. This graph is presented for illustrative purposes only and is not drawn to scale.
FIG. 3 graphically illustrates the natural passive immunity transfer mechanism operating under ideal conditions. This graph is presented for illustrative purposes only and is not drawn to scale.

Column 1, line 63, "FIG. 2 illustrates that" should be deleted.

Column 2, lines 16-19, "FIG. 3 charts calf blood serum Ig concentration versus time to illustrate the passive immunity transfer mechanism described above under absolutely ideal conditions which rarely occur in nature." should be deleted.

Column 2, lines 22-23, "as indicated by reference number 1" should be deleted.

Column 2, lines 28-29, "idly increases as indicated by the upwardly sloping line designated by reference number 2 At the time several" should be deleted and --idly increases. Several-- should be substituted.

Column 2, lines 30-31, "designated by reference number 3" should be deleted.

Column 2, line 36, "Following the time indicated by reference number 4" should be deleted and --Subsequently-- should be substituted.

UNITED STATES PATENT AND TRADEMARK OFFICE
CERTIFICATE OF CORRECTION

PATENT NO. : 4,816,252
DATED : March 28, 1989
INVENTOR(S) : Dr. Gerald H. Stott, Dr. David O. Lucas It is certified that error appears in the above-identified patent and that said Letters Patent is hereby corrected as shown below:

Column 2, lines 39-40, "By the time indicated by reference number 5" should be deleted and --Ultimately-- should be substituted.

Column 2, lines 50-61, "The dramatic contrast between an ideal immunity transfer as illustrated in FIG. 3 and common naturally occurring immunity transfer is illustrated in FIG. 4. Consumption of an insufficient quantity of colostrum or consumption of low Ig concentration colostrum as described in the following paragraph produces a passive immunity transfer curve analogous to that designated by reference number 6 in FIG. 4. If a calf having this deficient level of passive immunity is exposed to a disease, there is a high probability that it will contract the disease, require expensive medical treatment and may die or lack sufficient growth potential." and substitute --An ideal immunity transfer dramatically contrasts with a common naturally occurring immunity transfer. Consumption of an insufficient quantity of colostrum or consumption of a low Ig concentration colostrum produces a deficient level of passive immunity. If a calf having this deficient level of passive immunity is exposed to a disease, there is a high probability that it will contract the disease, require expensive medical treatment and may die or lack sufficient growth potential.--

UNITED STATES PATENT AND TRADEMARK OFFICE
CERTIFICATE OF CORRECTION

PATENT NO.   : 4,816,252
DATED        : March 28, 1989
INVENTOR(S)  : Dr. Gerald H. Stott, Dr. David O. Lucas It is certified that error appears in the above-identified patent and that said Letters Patent is hereby corrected as shown below:

Column 5, lines 23-52, beginning "FIG. 1 is a graph" and ending "pathogen specific antibodies." should be deleted.

Column 5, line 53, "7" should be deleted and --1-- should be substituted.

Column 5, line 58, "8" should be deleted and --2-- should be substituted.

Column 5, line 61, "9" should be deleted and --3-- should be substituted.

Column 5, line 64, "10" should be deleted and --4-- should be substituted.

Column 6, line 4, "11" should be deleted and --5-- should be substituted.

Column 6, line 13, "As indicated by FIG. 1, milk" should be deleted and --Milk-- should be substituted.

Column 6, lines 37-38, "The upper section of the FIG. 5 process flow chart indicates that in" should be deleted and --In-- should be substituted.

Column 7, line 12, "Referring now to FIG. 5, the" should be deleted and --The-- should be substituted.

Column 8, line 20, "in FIG. 5" should be deleted.

UNITED STATES PATENT AND TRADEMARK OFFICE
CERTIFICATE OF CORRECTION

PATENT NO. : 4,816,252

DATED : March 28, 1989

INVENTOR(S) : Dr. Gerald H. Stott, Dr. David O. Lucas

It is certified that error appears in the above-identified patent and that said Letters Patent is hereby corrected as shown below:

Column 8, lines 62-65, "Although the ultrafiltration modules depicted in FIG. 5 have been shown as having ultrafiltration membranes with either a ten thousand or one hundred thousand Dalton permeability," should be deleted and --Although a primary ultrafiltration process was described above in connection with a 10,000 Dalton membrane and a secondary ultrafiltration process was described above in connection with a 100,000 Dalton membrane,-- should be substituted.

Column 10, line 33 beginning "The graphs depicted" through line 52 ending "active filtered product" should be deleted and --The relative concentration of pathogen specific antibodies in various samples of dry filtered product produced by implementing the process of the present invention will have sample to sample variations resulting from the extraction of Ig molecules from different batches of raw milk having differing Ig distributions and concentrations.-- should be substituted.

Column 13, line 55, "Referring again to FIG. 5, the" should be deleted and --The-- should be substituted.

Column 13, line 58, beginning "FIG. 6A illustrates" through Column 14, line 3 ending "Thus, hen necessary," should be deleted and --When necessary-- should be substituted.

UNITED STATES PATENT AND TRADEMARK OFFICE
CERTIFICATE OF CORRECTION

PATENT NO. : 4,816,252
DATED : March 28, 1989
INVENTOR(S) : Dr. Gerald H. Stott, Dr. David O. Lucas It is certified that error appears in the above-identified patent and that said Letters Patent is hereby corrected as shown below:

Column 15, lines 64-65, "depicted in FIG. 5." should be deleted and --described above.-- should be substituted.

Column 16, lines 2-3, "The FIG. 5" should be deleted and --This-- should be substituted.

Column 19, line 11, "in connection with FIG. 2" should be deleted.

Column 19, line 50, "As indicated by FIG. 7, a" should be deleted and --A-- should be substituted.

Column 25, line 28, "11" should be deleted and --5-- should be substituted.

Column 26, line 1, "8" should be deleted and --2-- should be substituted.

Column 26, line 2, "depicted in FIG. 5" should be deleted and --described above-- should be substituted.

Column 26, lines 20-21, "in connection with FIG. 5" should be deleted.

Column 26, lines 42-43, "was the case in connection with the analogous material described with FIG. 5" should be deleted and --described-- should be substituted.

UNITED STATES PATENT AND TRADEMARK OFFICE
CERTIFICATE OF CORRECTION

PATENT NO. : 4,816,252

DATED : March 28, 1989

INVENTOR(S) : Dr. Gerald H. Stott, Dr. David O. Lucas

It is certified that error appears in the above-identified patent and that said Letters Patent is hereby corrected as shown below:

Column 26, line 48, after "described" insert --initially and--.

Column 26, line 49, "FIGS. 5 and 8" should be deleted and --FIG. 2-- should be substituted.

Column 27, line 1, "FIGS. 8, 9 and 10" should be deleted and --FIGS. 2, 3 and 4-- should be substituted.

Column 27, line 14, "FIG. 8" should be deleted and --FIG. 2-- should be substituted.

Column 27, line 17, "FIG. 10" should be deleted and --FIG. 4-- should be substituted.

Column 27, line 22, "FIG. 9" should be deleted and --FIG. 3-- should be substituted.

Column 27, line 25, "FIG. 9" should be deleted and --FIG. 3-- should be substituted.

Column 27, lines 26-27, "FIG. 8" should be deleted and --FIG. 2-- should be substituted.

Column 27, line 28, "FIG. 9" should be deleted and --FIG. 3-- should be substituted.

Column 27, line 29, "FIG. 8" should be deleted and --FIG. 2-- should be substituted.

UNITED STATES PATENT AND TRADEMARK OFFICE
CERTIFICATE OF CORRECTION

PATENT NO. : 4,816,252
DATED : March 28, 1989
INVENTOR(S) : Dr. Gerald H. Stott, Dr. David O. Lucas It is certified that error appears in the above-identified patent and that said Letters Patent is hereby corrected as shown below:

Column 27, line 35, "FIG. 8" should be deleted and --FIG. 2-- should be substituted.

Column 28, line 33, "FIG. 10" should be deleted and --FIG. 4-- should be substituted.

Column 28, line 34, "FIG. 8" should be deleted and --FIG. 2-- should be substituted.

Column 28, line 36, "FIG. 9" should be deleted and --FIG. 3-- should be substituted.

Column 29, line 3, "FIG. 9" should be deleted and --FIG. 3-- should be substituted.

Column 31, line 61, "25" should be deleted and --1-- should be substituted.

Signed and Sealed this

Tenth Day of April, 1990

Attest:

HARRY F. MANBECK, JR.

Attesting Officer    Commissioner of Patents and Trademarks